(12) United States Patent
Groves

(10) Patent No.: US 12,411,138 B2
(45) Date of Patent: Sep. 9, 2025

(54) ASSAYS WITH INDUCED AGGREGATION FOR ENHANCED SENSITIVITY

(71) Applicant: ILYTICA LLC, San Francisco, CA (US)

(72) Inventor: Jay T. Groves, San Francisco, CA (US)

(73) Assignee: ILYTICA LLC, San Francisco, CA (US)

( * ) Notice: Subject to any disclaimer, the term of this patent is extended or adjusted under 35 U.S.C. 154(b) by 802 days.

(21) Appl. No.: 17/226,989

(22) Filed: Apr. 9, 2021

(65) Prior Publication Data

US 2021/0318309 A1 Oct. 14, 2021

Related U.S. Application Data

(60) Provisional application No. 63/007,701, filed on Apr. 9, 2020.

(51) Int. Cl.
| | | |
|---|---|---|
| *G01N 33/569* | (2006.01) | |
| *A61B 8/00* | (2006.01) | |
| *G01N 15/14* | (2024.01) | |
| *G01N 21/64* | (2006.01) | |
| *G01N 21/77* | (2006.01) | |
| *G01N 33/53* | (2006.01) | |
| *G01N 33/545* | (2006.01) | |

(52) U.S. Cl.
CPC ..... *G01N 33/56966* (2013.01); *A61B 8/5223* (2013.01); *G01N 15/147* (2013.01); *G01N 21/64* (2013.01); *G01N 33/5304* (2013.01); *G01N 33/545* (2013.01); *G01N 2015/1477* (2013.01); *G01N 2021/6421* (2013.01); *G01N 2021/7786* (2013.01); *G01N 2333/4737* (2013.01)

(58) Field of Classification Search
None
See application file for complete search history.

(56) References Cited

U.S. PATENT DOCUMENTS

| | | |
|---|---|---|
| 7,169,556 B2 | 1/2007 | Park |
| 7,397,043 B2 | 7/2008 | Ja |
| 11,680,900 B2 | 6/2023 | Groves |
| 2003/0092029 A1 | 5/2003 | Josephson |
| 2006/0127946 A1 | 6/2006 | Montagu |
| 2009/0170070 A1 | 7/2009 | Neerken |
| 2009/0245652 A1 | 10/2009 | Bastos Dos Santos |
| 2009/0258371 A1 | 10/2009 | Wardlaw |
| 2010/0178208 A1 | 7/2010 | Caibin |
| 2010/0254588 A1 | 10/2010 | Cualing |
| 2010/0285490 A1 | 11/2010 | Dees |
| 2011/0097705 A1 | 4/2011 | Kachurin |
| 2013/0316467 A1 | 11/2013 | Carron |
| 2014/0193839 A1 | 7/2014 | Cunningham |
| 2014/0243223 A1 | 8/2014 | Duffy |
| 2014/0256593 A1 | 9/2014 | Szmacinski |
| 2015/0293084 A1 | 10/2015 | Del Pino González De La Higuera |
| 2019/0204313 A1 | 7/2019 | Huo |
| 2019/0293665 A1 | 9/2019 | Patel |
| 2020/0132600 A1 | 4/2020 | Groves |
| 2023/0258561 A1 | 8/2023 | Groves |

FOREIGN PATENT DOCUMENTS

| | | |
|---|---|---|
| CN | 109858605 | 6/2019 |
| EP | 2265931 | 12/2010 |
| JP | 2008157923 | 7/2008 |
| WO | 2008051287 | 5/2008 |
| WO | 2008055915 | 5/2008 |
| WO | 2009126505 | 10/2009 |
| WO | 2010033508 | 3/2010 |
| WO | 2011005754 | 1/2011 |
| WO | 2012117332 | 9/2012 |
| WO | 2016020391 | 2/2016 |
| WO | 2016046335 | 3/2016 |
| WO | 2016187588 | 11/2016 |
| WO | 2018169885 | 9/2018 |
| WO | 2020037289 | 2/2020 |
| WO | 2021207656 | 10/2021 |

OTHER PUBLICATIONS

Chenail, Gregg, et al. "Real-time analysis of antibody interactions with whole enveloped human cytomegalovirus using surface plasmon resonance." Analytical biochemistry 411.1 (2011): 58-63.*
International Application No. PCT/US2021/026660; International Preliminary Report on Patentability, date of mailing Oct. 20, 2022; 5 pages.
U.S. Appl. No. 16/493,237; Applicant-Initiated Interview Summary, dated Oct. 21, 2022; 2 pages.
U.S. Appl. No. 16/493,237; Examiner-Initiated Interview Summary, dated Jan. 11, 2023; 1 page.
U.S. Appl. No. 16/493,237; Non-Final Office Action, dated Aug. 2, 2022; 35 pages.
U.S. Appl. No. 16/493,237; Notice of Allowance, dated Feb. 2, 2023; 12 pages.
Xiao, L.. et al., "Single molecule biosensing using color coded plasmon resonant metal nanoparticles", Anal Chem., 82(14):6308-14, (2010).
Agrawal, A. et al., "Counting Single Native Biomolecules and Intact Viruses With Color-Coded Nanoparticles", Anal Chem., 78(4):1061-70, (2006).

(Continued)

*Primary Examiner* — G. Steven Vanni
(74) *Attorney, Agent, or Firm* — Global Patent Group Inc.; Cynthia Hathaway; Brock Levin

(57) ABSTRACT

Provided herein are systems, devices and methods for the rapid and accurate measurement of analyte particles binding-induced aggregation of reporter particles. In the presence of analyte particles of interest, reporter particles form aggregates which increase in mean particle size as the concentration of analyte increases. From analysis of the mean particle size, determined from sample frames, the presence and/or concentration of analyte can be determined.

23 Claims, 20 Drawing Sheets

(56) References Cited

OTHER PUBLICATIONS

Fazio B et al., SERS detection of Biomolecules at Physiological pH via aggregation of Gold Nanorods mediated by Optical Forces and Plasmonic Heating, Sci Rep Jun. 1, 2016;6:26952 pp. 1-13.

International Application No. PCT/US2018/022061; International Preliminary Report on Patentability, date of issuance Sep. 26, 2019; 12 pages.

International Application No. PCT/US2018/022061; International Search Report and Written Opinion of the International Searching Authority, date of mailing Mar. 12, 2018; 28 pages.

International Application No. PCT/US2021/026660; International Search Report and Written Opinion of the International Searching Authority, date of mailing, Jul. 28, 2021, 7 pages.

Levene, M. et al., "Zero-Mode Waveguides for Single-Molecule Analysis at High Concentrations", Science, 299 (5607):682-6, (2003).

Schultz, S. et al., "Single-Target Molecule Detection With Nonbleaching Multicolor Optical Immunolabels", Proc Natl Acad Sci USA, 97(3):996-1001, (2000).

Walt, D., "Optical Methods for Single Molecule Detection and Analysis", Anal Chem., 85(3):1258-63, (2013).

Fu, Y. et al., "Cytomorphology-based microchip with contour extraction processing for bioparticle analysis", Electophoresis, 40:1195-1201, (2019).

\* cited by examiner (a)

(b)

(a)

(b)

(a)

(b)

(c)

(a)

(b)

(c)

(a)

(b)

(c)

(a)

(b)

(a)

(b)

(a)

(b)

(c)

ASSAYS WITH INDUCED AGGREGATION FOR ENHANCED SENSITIVITY

This application claims the benefit of priority of United States Provisional Application No. 63/007,701, filed Apr. 9, 2020, the disclosure of which is hereby incorporated by reference as if written herein in its entirety.

Point-of-care diagnostics and other assays performable in the field are a pressing need. If the delay and expense associated with sending assays such as diagnostic tests, especially blood tests, to dedicated laboratories for analysis could be eliminated, responses could be made more efficiently and effectively. Clinical laboratories deliver diagnostic tests by performing biochemical assays on precision, benchtop instruments. Efforts to miniaturize these instruments or replicate their function on mobile electronic devices are fraught with difficulty. In many cases the results are unusable.

What are needed are inexpensive, but accurate, point-of-care assays such as diagnostic tests that provide quick and accurate results, for example doctors and their patients.

BRIEF DESCRIPTION OF THE DISCLOSURE

Provided herein are systems, devices and methods for the rapid and accurate measurement of analyte particles by assay of binding events. The sensor devices contain one or more types of reporter particles which comprise macromolecular or nanoscale components, such as nanoparticles. The reporter particles (or alternately, "reporters") produce a large enough optical signal so that individual reporter particles can be imaged, and appear in sample frames as individually detectable objects. In the presence of an analyte (e.g. molecule, viral particles, or bacterium) of interest, the reporter particles form aggregates containing multiple reporter particles, and which thus appear in sample frames as larger objects. As concentration of analyte increases, the degree of aggregation and the size of aggregates both increase. From features discernable in the images such as mean object size, perimeter, shape, color, etc. determined from sample image frames, the presence and/or concentration of analyte can be determined. Key to this detection strategy is the application of image processing and filtering procedures designed to remove error and noise from the images and select viable objects for analysis prior to summing the results to determine analyte concentration.

Provided herein is a method for determining the presence or concentration of an analyte particle in a sample, comprising the steps of:
combining the sample with a quantity of one or more types of reporter particles in a detector volume;
recording one or more frames of the detector volume;
identifying, in the one or more frames, images of objects corresponding to aggregates of reporter particles and, optionally, individual un-aggregated reporter particles;
determining one or more object characteristics; and
from the object characteristics, determining the presence and/or concentration of the analyte;
wherein:
the presence of analyte induces the formation of aggregates, each comprising at least two of the reporter particles, and at least one analyte particle.

DETAILED DESCRIPTION OF THE DISCLOSURE

Figure 1:
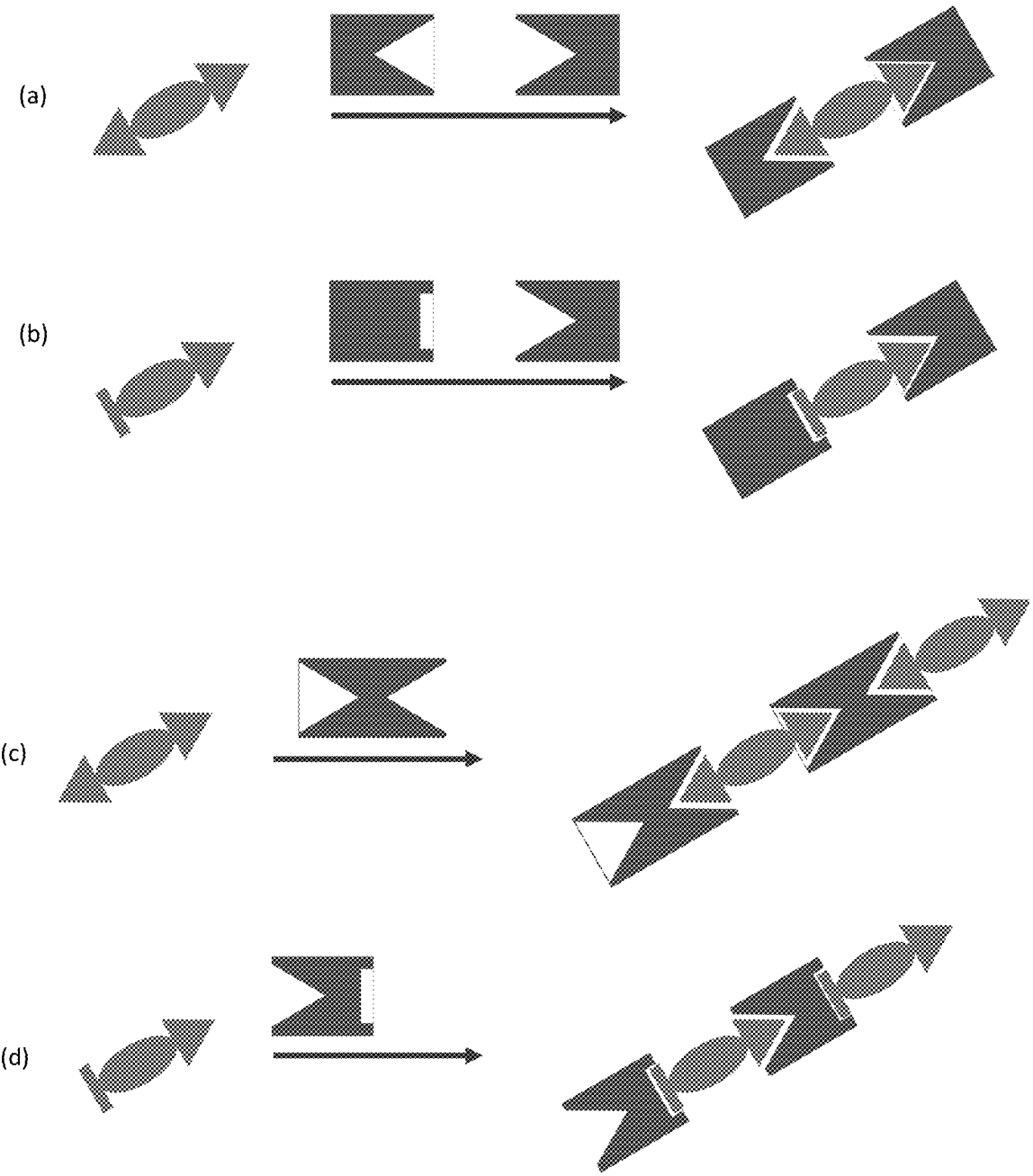
FIG. 1 shows the design principle for reporter particles with 2 binding sites.

The disclosure is directed at methods to perform biochemical assays with improved speed, accuracy, precision, and affordability. The methods utilize an aggregation process whereby the binding of analyte particles of interest by multiple reporter particles induces aggregation into macromolecular assemblies, facilitating direct imaging by readily available optical devices.

There is great demand for performing biochemical assays on mobile electronic devices, which has the potential to improve the speed, accuracy, sensitivity, and affordability of diagnostic tests. Substantial technology exists for capturing two-dimensional (X/Y) images of a three-dimensional object. Technology has advanced from film-based cameras through video cameras, image plates, charge-coupled devices, and complementary metal oxide ("CMOS") chips. Such images are the projection of the three-dimensional object onto a two-dimensional plane. Generally, a two-dimensional frame is subdivided into picture units termed pixels for processing and downstream manipulation, which can be conveniently referenced through a two-coordinate addressing system. By way of example, a square frame can be subdivided into a 512×512 array of tiles, each of which can be addressed by an ordered pair of integers (x,y), where both x and y can range from 1 to 512, inclusive.

Observation of common "small molecule" organic compounds and smaller biomolecules in solution is not generally feasible for two reasons: (a) the spatial resolution of detectors is much coarser than size of these small molecules, so that each pixel captures the signal from a large number of solute molecules, and (b) the signal from individual molecules of this size is generally too weak for detection above noise. Although work has been performed to image individual molecules, procedures to date are generally slow, tedious, and/or expensive. In contrast, technology is available to image solutes of nanometer scale or larger, due both to the larger particle size, and to the enhanced signal that is often available from these larger particles.

The present disclosure solves the problem of poor signal-to-noise for analyte particles by utilizing reporter particles comprising macromolecular or nanoscale components, such as nanoparticles. The reporter particles (or alternately, "reporters") are large enough so that individual reporter particles can be imaged, and, in some embodiments, appear in sample frames as particles having finite size. In the presence of an analyte particle of interest, the reporter particles form aggregates containing multiple reporters, and which thus appear in sample frames as larger particles. As concentration of analyte increases, the degree of aggregation and the size of aggregates both increase. From the mean particle size, determined from sample frames, the presence and/or concentration of analyte can be determined.

Provided herein is Embodiment 1: a method for determining the presence or concentration of an analyte particle in a sample, comprising the steps of:
combining the sample with a quantity of one or more types of reporter particles in a detector volume;
recording one or more frames of the detector volume;
identifying, in the one or more frames, images of objects corresponding to aggregates of reporter particles and, optionally, individual un-aggregated reporter particles;
determining one or more object characteristics; and
from the object characteristics, determining the presence and/or concentration of the analyte;
wherein:
the presence of analyte induces the formation of aggregates, each comprising at least two of the reporter particles, and at least one analyte particle.

Also provided are the following embodiments:

Embodiment 2: the method of Embodiment 1 wherein the images of particles correspond to aggregates of reporter particles and individual un-aggregated reporter particles.

Embodiment 3: the method of Embodiment 1 wherein the images of particles correspond to aggregates of reporter particles.

Embodiment 4: the method of any one of Embodiments 1-3 wherein each of the one or more frames consists of an array of pixels.

Embodiment 5: the method of any one of Embodiments 1-4 wherein formation of aggregates is caused by binding between a binding site on at least one of the one or more types of reporter particles and a binding site on the analyte particle.

Embodiment 6: the method of Embodiment 1 wherein each of the one or more types of reporter particles comprises a nanoparticle or quantum dot.

Embodiment 7: the method of Embodiment 6 wherein each of the one or more types of reporter particles comprises a nanoparticle.

Embodiment 8: the method of Embodiment 7 wherein each of the one or more types of reporter particles comprises a gold nanoparticle ("GNP").

Embodiment 9: the method of any one of Embodiments 1-8 wherein each of the one or more types of reporter particles contains two or more binding sites.

Embodiment 10: the method of Embodiment 9 wherein each of the one or more types of reporter particles contains two or more of the same type of binding site.

Embodiment 11: the method of Embodiment 9 wherein at least one of the one or more types of reporter particles contains two or more non-identical binding sites.

Embodiment 12: the method of either of Embodiments 10 and 11 wherein at least one type of binding site is located on an antibody or nanobody contained in a reporter particle.

Embodiment 13: the method of Embodiment 12 wherein at least one type of binding site is located on an antibody contained in a reporter particle.

Embodiment 14: the method of either one of Embodiments 12 and 13 wherein at least one type of binding site is located on a nanobody contained in a reporter particle.

Embodiment 15: the method of Embodiment 9 wherein the one or more types of reporter particles is a single type of reporter particle.

Embodiment 16: the method of Embodiment 15 wherein the single type of reporter particle contains a single type of binding site.

Embodiment 17: the method of Embodiment 16 wherein the single type of binding site is located on an antibody or nanobody contained in the single type of reporter particle.

Embodiment 18: the method of Embodiment 17 wherein the single type of binding site is located on an antibody contained in the single type of reporter particle.

Embodiment 19: the method of Embodiment 17 wherein the single type of binding site is located on a nanobody contained in the single type of reporter particle.

Embodiment 20: the method of any one of Embodiment 15-19 wherein the single type of reporter particle can bind simultaneously to two or more analyte particles.

Embodiment 21: the method of any one of Embodiment 15-20 wherein the analyte particle can bind simultaneously to two or more reporter particles.

Embodiment 22: the method of Embodiment 9 wherein the one or more types of reporter particles is two types of reporter particles.

Embodiment 23: the method of Embodiment 22 wherein each of the one or more types of reporter particles contains one or more of the same type of binding site.

Embodiment 24: the method of Embodiment 23 wherein each of the two types of reporter particles contains a different type of binding site from the other type of reporter particle.

Embodiment 25: the method of Embodiment 24 wherein each of the two types of different binding sites is located on an antibody or nanobody contained in each of the two types of reporter particle.

Embodiment 26: the method of Embodiment 25 wherein at least one of the two types of different binding sites is located on an antibody contained in one of the two types of reporter particle.

Embodiment 27: the method of Embodiment 26 wherein the two types of different binding sites are located on antibodies contained in the two types of reporter particle.

Embodiment 28: the method of either one of Embodiments 25 and 26 wherein at least one of the two types of different binding sites is located on a nanobody contained in one of the two types of reporter particle.

Embodiment 29: the method of Embodiment 25 wherein the two types of different binding sites are located on nanobodies contained in the two types of reporter particle.

Embodiment 30: the method of any one of Embodiments 22-29 wherein each of the two types of reporter particles can bind simultaneously to two or more analyte particles.

Embodiment 31: the method of any one of Embodiments 22-30 wherein the analyte particle can bind simultaneously to one or more of each of the two types of reporter particles.

Embodiment 32: the method of any one of Embodiments 13, 18, and 26 wherein at least one binding site is located on a human antibody contained in a reporter particle.

Embodiment 33: the method of any one of Embodiments 13, 18, and 26 wherein at least one binding site is located on an anti-human antibody contained in a reporter particle.

Embodiment 34: the method of any one of Embodiments 13, 18, and 26 wherein at least one binding site is located on an anti-C-reactive protein contained in a reporter particle.

Embodiment 35: the method of Embodiment 34 wherein at least one binding site is located on a C2 anti-C-reactive protein contained in a reporter particle.

Embodiment 36: the method of Embodiment 34 wherein at least one binding site is located on a C6 anti-C-reactive protein contained in a reporter particle.

Embodiment 37: the method of any one of Embodiments 9-36 wherein at least one binding site is located on a biomolecule contained in a reporter particle.

Embodiment 38: the method of Embodiment 37 wherein the biomolecule is from the protein viral envelope of a virus.

Embodiment 39: the method of Embodiment 38 wherein the biomolecule is chosen from a membrane protein, an envelope protein, and a spike protein.

Embodiment 40: the method of Embodiment 39 wherein the biomolecule is a spike protein from the protein viral envelope of a virus.

Embodiment 41: the method of any one of Embodiments 38-40 wherein the virus is a coronavirus.

Embodiment 42: the method of Embodiment 41 wherein the virus is SARS-CoV-2.

Embodiment 43: the method of any one of Embodiments 1-42 wherein the analyte particle is an antibody.

Embodiment 44: the method of Embodiment 43 wherein the analyte is an antibody to a biomolecule in the viral envelope of a virus.

Embodiment 45: the method of Embodiment 44 wherein the analyte is an antibody to a biomolecule in the viral envelope of a virus chosen from a membrane protein, an envelope protein, and a spike protein.

Embodiment 46: the method of Embodiment 45 wherein analyte is an antibody to a spike protein.

Embodiment 47: the method of Embodiment 46 wherein analyte is an antibody to the spike protein of SARS-CoV-2.

Embodiment 48: the method of any one of Embodiments 1-36 wherein the analyte is a hematological protein.

Embodiment 49: the method of Embodiment 48 wherein the hematological protein is C-reactive protein ("CRP").

Embodiment 50: the method of any one of Embodiments 1-42 wherein the analyte is chosen from a virus, an archaeum, and a bacterium.

Embodiment 51: the method of Embodiment 50 wherein the analyte is a virus.

Embodiment 52: the method of Embodiment 51 wherein the analyte is a coronavirus.

Embodiment 53: the method of Embodiment 52 wherein the analyte is SARS-CoV-2. In certain embodiments, the binding site binds to a spike protein.

Embodiment 54: the method of any one of Embodiments 1-42 wherein the analyte is a bacterium.

Embodiment 55: the method of Embodiment 54 wherein binding site binds to a surface glycoprotein on the bacterium.

Embodiment 56: the method of any one of Embodiments 1-55 wherein the analyte particle contains two or more binding sites.

Embodiment 57: the method of Embodiment 56 wherein the analyte particle contains two or more identical binding sites.

Embodiment 58: the method of Embodiment 56 wherein the analyte particle contains two or more non-identical binding sites.

Embodiment 59: the method of any one of Embodiments 1-58 wherein the object characteristic permits the separation, by the setting of pre-determined limit in an algorithm used to process and filter the images of the objects, of noise, artifacts, unusable image features, and/or background from signal corresponding to analyte.

Embodiment 60: the method of Embodiment 59 wherein the object characteristic permits the separation, by the setting of pre-determined limit in an algorithm used to process and filter the images of the objects, of noise from signal corresponding to analyte.

Embodiment 61: the method of either one of Embodiments 59 and 60 wherein the object characteristic permits the separation, by the setting of pre-determined limit in an algorithm used to process and filter the images of the objects, of artifacts from signal corresponding to analyte.

Embodiment 62: the method of any one of Embodiments 59-61 wherein the object characteristic permits the separation, by the setting of pre-determined limit in an algorithm used to process and filter the images of the objects, of unusable image features from signal corresponding to analyte.

Embodiment 63: the method of any one of Embodiments 59-62 wherein the object characteristic permits the separation, by the setting of pre-determined limit in an algorithm used to process and filter the images of the objects, of background from signal corresponding to analyte.

Embodiment 64: the method of any one of Embodiments 1-63 wherein the object characteristic enables the removal, by the setting of pre-determined limits in an algorithm used to process and filter the images of the objects, of one or more images of non-analyte particles, one or more unusable images, and/or one or more background features.

Embodiment 65: the method of Embodiment 64 wherein the object characteristic enables the removal, by the setting of pre-determined limits in an algorithm used to process and filter the images of the objects, of one or more images of non-analyte particles.

Embodiment 66: the method of either one of Embodiments 64 and 65 wherein the object characteristic enables the removal, by the setting of pre-determined limits in an algorithm used to process and filter the images of the objects, of one or more unusable images.

Embodiment 67: the method of any one of Embodiments 64-66 wherein the object characteristic enables the removal, by the setting of pre-determined limits in an algorithm used to process and filter the images of the objects, of one or more background features.

Embodiment 68: the method of any one of Embodiments 1-67 wherein the object characteristic increases monotonically with aggregate size.

Embodiment 69: the method of Embodiment 68 wherein the object characteristic increases proportionally to aggregate size.

Embodiment 70: the method of either one of Embodiments 68 and 69 wherein the object characteristic is related to the median size of the aggregate.

Embodiment 71: the method of either one of Embodiments 68 and 69 wherein the object characteristic is related to the mean size of the aggregate.

Embodiment 72: the method of either one of Embodiments 68 and 69 wherein the object characteristic is related to the RMS size of the aggregate.

Embodiment 73: the method of any one of Embodiments 1-72 wherein the mean aggregate size can be determined from the object characteristic by means of a calibration curve.

Embodiment 74: the method of Embodiment 73 wherein the method further comprises the step of obtaining a calibration curve.

Embodiment 75: the method of any one of Embodiments 1-74 wherein the object characteristic is chosen from the size of the aggregate, as directly observed or estimated, the perimeter of the aggregate, as directly observed or estimated, the area of the aggregate, as directly observed or estimated, the shape of the aggregate, the color of the aggregate, the brightness of the aggregate, the reflectivity of the aggregate, the fluorescence of the aggregate, and the phosphorescence of the aggregate.

Embodiment 76: the method of Embodiment 75 wherein the object characteristic is chosen from the size of the aggregate, as directly observed or estimated, the perimeter of the aggregate, as directly observed or estimated, and the area of the aggregate, as directly observed or estimated.

Embodiment 77: the method of Embodiment 75 wherein the object characteristic is chosen from the brightness of the aggregate, the fluorescence of the aggregate, and the phosphorescence of the aggregate.

Embodiment 78: the method of Embodiment 77 wherein the object characteristic is the brightness of the aggregate.

Embodiment 79: the method of any one of Embodiments 1-78 wherein the one or more types of reporter particles provides an optical signal.

Embodiment 80: the method of Embodiment 79 wherein the optical signal is chosen from UV/Vis absorbance, fluorescence emission, and phosphorescence emission.

Embodiment 81: the method of Embodiment 79 the optical signal is substantially unchanged upon binding of reporter particle to analyte particle.

Embodiment 82: the method of Embodiment 79 the optical signal is caused by surface plasmon resonance ("SPR").

Embodiment 83: the method of Embodiment 82 the surface plasmon resonance is localized surface plasmon resonance.

Embodiment 84: the method of any one of Embodiments 1-83 further comprising the step of removing background features.

Embodiment 85: the method of Embodiment 84 further comprising the step of removing background features greater than a given size maximum.

Embodiment 86: the method of either one of Embodiments 84 and 85 further comprising the step of removing background features smaller than a given size minimum.

Embodiment 87: the method of any one of Embodiments 1-86 further comprising the steps of:
eroding an image;
reconstructing an image; and
dilating an image.

Embodiment 88: the method of any one of Embodiment 1-87 further comprising one or more steps of border formation in the one or more frames of the detector volume.

Embodiment 89: the method of method of any one of Embodiment 1-88 wherein the sample is a biological fluid.

Embodiment 90: the method of Embodiment 89 wherein the sample is a biological fluid that has been diluted, concentrated, and/or pre-treated.

Embodiment 91: the method of either one of Embodiments 89 and 90 wherein In certain embodiments, the sample is derived from blood.

Embodiment 92: the method of Embodiment 91 wherein the sample contains intact blood cells.

Embodiment 93: the method of Embodiment 92 wherein the sample contains intact red blood cells.

Embodiment 94: the method of any one of Embodiments 1-93 wherein the sample is analyzed with a microscope.

Embodiment 95: the method of Embodiment 94 wherein the sample is analyzed with a microscope capable of darkfield imaging.

Embodiment 96: the method of either one of Embodiments 94 and 95 wherein the microscope is capable of brightfield imaging.

Embodiment 97: the method of any one of Embodiments 94-96 wherein the microscope is capable of autofocus.

Embodiment 98: the method of any one of Embodiments 94-97 wherein the microscope comprises a fluorescence illuminator.

Embodiment 99: the method of any one of Embodiments 94-98 wherein the fluorescence illuminator comprises a fly-eye lens.

Embodiment 100: the method of any one of Embodiments 1-99 wherein the optical path length is no more than 0.1 mm thick.

Embodiment 101: the method of Embodiment 100 wherein the optical path length is no more than 0.05 mm thick.

Embodiment 102: the method of Embodiment 101 wherein the optical path length is no more than 0.02 mm thick.

Embodiment 103: the method of Embodiment 102 wherein the optical path length is no more than 0.01 mm thick.

Embodiment 104: the method of any one of Embodiments 1-103 wherein the sample is processed with a microfluidic apparatus.

Also provided is Embodiment 105: an apparatus or system for performing a method of any one of Embodiments 1-104 comprising:
an image sensor;
a screen capable of displaying an image;
a microprocessor;
memory;
image analysis software stored in the memory and executable by the processor capable of analyzing the data captured by the image sensor and digitally classifying data; and
optionally, a communication interface.

Also provided are the following embodiments:

Embodiment 106: The apparatus of Embodiment 105 further comprising a communication interface.

Embodiment 107: The apparatus of Embodiment 106 wherein the communication capability is wireless.

Embodiment 108: The apparatus of either one of Embodiments 106 and 107 wherein the apparatus or system can communicate with a smartphone or tablet computer.

Embodiment 109: The apparatus of either one of Embodiments 106 and 107 wherein the apparatus or system can communicate with a computer, smartphone or tablet computer.

Embodiment 110: The apparatus of any one of Embodiments 105-109 wherein the image sensor is capable of operating as part of a dark-field microscope.

Embodiment 111: The apparatus of any one of Embodiments 105-110 wherein the image sensor is capable of operating as part of a bright-field microscope.

Embodiment 112: The apparatus of any one of Embodiments 105-111 wherein the image sensor comprises a camera.

Embodiment 113: The apparatus of Embodiment 112 wherein the camera is a complementary metal-oxide semiconductor (CMOS) camera.

Embodiment 114: The apparatus of any one of Embodiments 105-113 further comprising a source of light or other electromagnetic radiation.

Embodiment 115: The apparatus of Embodiment 114 wherein the source of light or other electromagnetic radiation comprises a light-emitting diode (an LED).

Embodiment 116: The apparatus of either one of Embodiments 114 and 115 wherein the source of light or other electromagnetic radiation comprises a fish-eye lens.

Embodiment 117: The apparatus of any one of Embodiments 105-116 further comprising a sample chamber that is optionally removable.

Embodiment 118: The apparatus of any one of Embodiments 105-116 further comprising a reporter surface made of glass or polymer, to one side of which reporter particles comprising plasmonic nanoparticles functionalized with capture elements have been affixed.

Embodiment 119: The apparatus of Embodiment 118 further comprising a waveguide that is suitable for dark-field microscopy in contact with the opposite side of the reporter surface.

Embodiment 120: The apparatus of either one of Embodiments 118 and 119 wherein the reporter particles are optical reporter particles.

Embodiment 121: The apparatus of Embodiment 120 wherein each affixed optical reporter particle is spatially resolvable.

Embodiment 122: The apparatus of Embodiment 121 wherein the affixed optical reporter particles are arrayed randomly.

Embodiment 123: The apparatus of Embodiment 121 wherein the affixed optical reporter particles are arrayed in a grid or an approximation thereof.

Embodiment 124: The apparatus of any one of Embodiments 121-123 wherein each affixed optical reporter particles is resolvable as one pixel of a recording device.

Embodiment 125: The apparatus of any one of Embodiments 118-124 wherein the capture element is chosen from:
one or more nanobodies that binds the analyte;
one or more nucleotide sequences binds the analyte; and
an antibody or a fragment thereof that binds the analyte.

Embodiment 126: The apparatus of any one of Embodiments 105-125 wherein the apparatus or system can be used to perform a method as described herein for determining the presence or concentration of an analyte in a sample.

Embodiment 127: The apparatus of Embodiment 126 wherein the apparatus or system can be used to perform a method as described herein for determining the presence of an analyte in a sample.

Embodiment 128: The apparatus of Embodiment 126 wherein the apparatus or system can be used to perform a method as described herein for determining the concentration of an analyte in a sample.

Embodiment 129: The apparatus of any one of Embodiments 126-128 wherein the analyte is an antibody.

Embodiment 130: The apparatus of Embodiment 129 wherein the analyte is an antibody to a virus.

Embodiment 131: The apparatus of Embodiment 130 wherein the analyte is an antibody to a coronavirus.

Embodiment 132: The apparatus of Embodiment 131 wherein the analyte is an antibody to SARS-CoV-2.

Embodiment 133: The apparatus of any one of Embodiments 126-128 wherein the analyte is an antigen.

Embodiment 134: The apparatus of any one of Embodiments 126-128 wherein the analyte is chosen from a virus, an archaeum, and a bacterium.

Embodiment 135: The apparatus Embodiment 134 wherein the analyte is a virus.

Embodiment 136: The apparatus Embodiment 136 wherein the analyte is a coronavirus.

Embodiment 137: The apparatus Embodiment 135 wherein the analyte is a SARS-CoV-2.

Embodiment 138: The apparatus of any one of Embodiments 126-128 wherein the analyte is a nucleotide sequence.

Embodiment 139: The apparatus of any one of Embodiments 105-138 wherein the apparatus or system can be used to perform one or more of the following:
eroding an image;
reconstructing an image; and
dilating an image.

Embodiment 140: The apparatus of Embodiment 139 wherein the apparatus or system can be used to perform two or more of the following:
- eroding an image;
- reconstructing an image; and
- dilating an image.

Embodiment 141: The apparatus of Embodiment 140 wherein the apparatus or system can be used to perform all of the following:
- eroding an image;
- reconstructing an image; and
- dilating an image.

Embodiment 142: The apparatus of any one of Embodiments 105-141 wherein the apparatus or system can be used to perform one or more steps of border formation in an image.

Embodiment 143: The apparatus of any one of Embodiments 105-142 wherein the apparatus or system is all comprised within a single device.

Embodiment 144: The apparatus of Embodiment 143 wherein the apparatus or system are all comprised within a single, portable device.

Embodiment 145: The apparatus of either one of Embodiments 143 and 144 wherein the apparatus or system further comprises a case for positioning the smartphone, sample chamber, and light source in close and stable proximity to each other.

Embodiments disclosed herein are further intercombinable with each other, provided the combination is not mutually exclusive.

Terms and Definitions

Unless defined otherwise, all technical and scientific terms used herein have the same meaning as commonly understood by one of ordinary skill in the art to which this invention belongs.

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "accuracy", as used herein, alone or in combination, is used to refer to the closeness of a reported or estimated value from the true value. An inaccurate measurement, observation, or estimation deviates from the true value. An accurate measurement, observation, or estimation does not deviate from the true value.

The term "aggregate", as used herein, alone or in combination, is used to describe an assembly comprising at least one reporter particle and at least one analyte particle. In some embodiments, the term "aggregate" is reserved for an assembly comprising five or more total particles (reporter particle and analyte particle). In some embodiments, the term "aggregate" is reserved for an assembly comprising 10 or more total particles. In some embodiments, the term "aggregate" is reserved for an assembly comprising 20 or more total particles. In some embodiments, the term "aggregate" is reserved for an assembly comprising 50 or more total particles.

The term "analyte molecule", as used herein, alone or in combination, is used to describe a molecule or particle for which the presence or absence, or amount, in a sample is originally unknown, and for which knowledge of the presence or absence, or amount, contained in a sample would be useful. Examples of analyte molecules include biomolecules, such as: peptides, proteins, cytokines, and prions; antibodies, and fragments thereof; nucleic acids (DNA/RNA) and particles containing them, such as histones; small organic and bioinorganic molecules, such as carbohydrates, lipids, hormones, and intermediates and products of metabolism; macromolecules, such as macrocycles, biopolymers (e.g. oligosaccharides, polyphenols, and plastics); and viruses, viral particles, viral products (e.g. virokines).

The term "analyte particle", as used herein, alone or in combination, is used to embrace "analyte molecule", as described above, and larger particles for which the presence or absence, or amount, in a sample is originally unknown, and for which knowledge of the presence or absence, or amount, contained in a sample would be useful. Examples of analyte particles include viruses; prokaryotes, including bacteria and archaea; protists, including amoebas, choanaflagellates, ciliates, diatoms, dinoflagellates, Giardia, Plasmodium, and oomycetes.

An analyte particle may also be categorized as a biomarker, that is, a composition and/or molecule or a complex of compositions and/or molecules that is associated with a biological state of an organism (e.g., a condition such as a disease or a non-disease state) and can report the presence of disease, injury, or cellular or organismal damage. When such markers bind to an antibody or a fragment thereof, they may be referred to as antigens. Values for meaningful (e.g., normal and abnormal) levels of analyte particle detected by the aggregation assays disclosed herein will be known to those of skill in the relevant art.

The term "analyte" can refer to a certain type of substance composed of analyte particles, e.g., codeine, leukotriene, or PSA. The term "analyte" can also refer to an amount or concentration of analyte particles. The term "analyte" can also refer to a number of analyte particles. In certain usages, as will be evident from the context, the term "analyte" can refer to a single analyte particle.

The term "area detector", as used herein, alone or in combination, refers to a recording device that can record an image from a source, i.e., record not only the intensity of an incoming optical signal, but the origin of an optical signal. Common examples of area detectors are television cameras, digital SLR cameras, and cellphone cameras.

The term "binding", as used herein, alone or in combination, refers to a noncovalent interaction between reporter particle and analyte particle. In some embodiments, the binding is due to hydrogen bonding. In some embodiments, the binding is due to van der Waals interactions. In some embodiments, the binding is due to electrostatic and/or dipolar interactions. In some embodiments, the binding is due to a combination of one or more of the abovementioned interactions. In some embodiments, the binding corresponds to a dissociation constant of 1 mM or smaller. In some embodiments, the binding corresponds to a dissociation constant of 1 µM or smaller. In some embodiments, the binding corresponds to a dissociation constant of 1 nM or smaller.

The term "binding isotherm", as used herein, alone or in combination, refers to binding behavior of the reporter particle/analyte particle system. For a system in which both reporter particle and analyte has a single binding site (and for which formation of aggregates is therefore not possible), the term "binding isotherm" refers simply to the ratio of bound reporter particles/total reporter particles. It will be understood that this ratio will increase with increased analyte particle concentration, and eventually approaches 1, as nearly all reporter particles are bound to analyte particles. This behavior will also obtain when either the reporter particle or the analyte has a single binding site, since aggregation (which requires multiple binding for both reporter particle and analyte particle) is not possible. When both reporter particle and analyte particle have multiple binding sites, the number and particle size is also included in the binding isotherm.

The term "binding site", as used herein, alone or in combination, refers to a feature in either of the reporter particle or the analyte particle, which can form a noncovalent bond with a binding partner, thus holding the particle and binding partner in proximity. In some embodiments, a binding site on a reporter particle will bind exclusively with a binding site on an analyte particle. In some embodiments, a binding site on an analyte particle will bind exclusively with a binding site on a reporter particle. Certain reporter particles and certain analyte particles contain a single binding site. Certain reporter particles and certain analyte particles contain two binding sites. Certain reporter particles and certain analyte particles contain two or more binding sites. Certain reporter particles and certain analyte particles contain two identical binding sites. Certain reporter particles and certain analyte particles contain two non-identical binding sites. Certain reporter particles and certain analyte particles contain two or more identical binding sites. Certain reporter particles and certain analyte particles contain two or more non-identical binding sites. In some embodiments, either of the reporter particle or analyte contains a plurality of binding sites. In some embodiments, binding behavior of each of the plurality of binding sites is uncorrelated with each of the remainder of the binding sites; stated differently, the likelihood of one binding site forming a noncovalent bond with a partner is unaffected by the presence or absence of noncovalent bonds formed by other binding sites on the same particle.

The term "binning", as used herein, alone or in combination, refers to the combination of signals from two or more pixels into one signal. Binning can be used when spatial resolution can be sacrificed in order to improve signal-to-noise. "2×2 binning", by way of example, refers to the grouping of pixels into 2×2 squares, and summing the signals from the pixels contained in each square.

The term "biomolecule", as used herein, alone or in combination, includes any type of organic or bioinorganic molecule for which detection (either qualitative or quantitative) may be desired, including but not limited to, peptides, proteins, nucleic acids, sugars, mono- and polysaccharides, lipids, lipoproteins, whole cells, and the like.

The term "camera," as used herein, refers to a type of image sensor for recording visual images, for example as digital frames. A "megapixel camera" is a camera that can record one million, or multiples of one million, pixels per frame. Many smartphone cameras comprise ten-megapixel or more cameras.

The term "communication interface," as used herein, refers to a means for transferring data from a device or system as used herein to another device or system. Examples of wireless communications interfaces include those used in wireless devices such as mobile phones, for example cellular, wi-fi, and Bluetooth technologies.

The term "clinical use", as used herein, alone or in combination, is used to describe methods for analysis of samples containing an unknown concentration of analyte particle. The term "clinical use" is intended to differentiate from "non-clinical use". Clinical use includes, but is not limited to, use for the determination of analyte particle concentrations in patients in a medical setting. The term "non-clinical use", as used herein, alone or in combination, is used to describe methods for analysis of samples containing a known concentration of analyte particle. Non-clinical use includes, but is not limited to, measurement of samples for the determination of behavior of devices and methods at well-defined analyte particle concentrations. Non-clinical use embraces both pre-clinical use and post-clinical use.

The term "concentration", as used herein, alone or in combination, refers to the amount of a solute in a solution per unit volume of solution. Concentration can be specified in units of molar concentration, i.e. number of moles of solute per liter of solution, or number concentration, i.e., number of molecules of solute per liter of solution or, alternatively, number of particles of solute per liter of solution. Molar concentration and number concentration can be readily interconverted. As used herein, the term "concentration" is expanded to include systems outside the traditional definition of "solution", e.g., systems containing molecules tethered to a solid support, and particles that are outside the traditional definition of "molecule", i.e., viruses and microorganisms.

The term "detect" or "detection", as used herein, alone or in combination, is used to describe a method of determination of the existence, presence, or fact of an analyte particle in a sample.

The term "divergence" indicates the deviation from perpendicularity that is accommodated by the recording device. An idealized area-detector type recording device will accept only light rays that are perpendicular to the plane of the detector. Actual area detectors will allow light rays that arrive at an angle from the perpendicular. Although this feature can increase signal-to-noise (since more light rays are accepted by the detector), it also decreases spatial resolution, depending on the size of the divergence angle allowed, and the size of the area detector pixel and distance between the area detector and the sample plane.

The term "frame", as used herein, alone or in combination, refers to the substantial entirety of the image captured by a recording device. Certain cameras capture one frame at a time. Certain cameras capture a sequence of frames over a period of time.

The term "image", as used herein, alone or in combination, refers to a feature in a camera signal that is due to a particular object being captured by a recording device. For example, the image of the Moon can be captured in a camera mounted to a telescope, and the image of a customer can be captured in an ATM camera. In some contexts, the term "image" refers to the entirety of the camera signal without regard to the origin of the signal. The meaning of the term will be apparent from the context.

The term "incubate", as used herein, alone or in combination, is used to describe a process of exposing reporter particles to a sample that can potentially contain an analyte particle.

The term "oblong" as used herein, alone or in combination, is used to describe a volume having unequal dimensions. Examples of oblong volumes include prisms or cylinders for which the distance between the end faces is either significantly larger or significantly smaller than dimensions parallel to the end faces. A further example of an oblong volume is an ellipsoid for which one axis is either significantly larger or significantly smaller than the other axes.

The term "optical path", as used herein, alone or in combination, is used to describe the path from reporter particle to detector.

The term "optical reporter particle," or, equivalently, "optical reporter," as used herein, alone or in combination, is used to describe a reporter particle that is capable of reporting either the presence or absence, or the amount or concentration of, an analyte particle, with an optical signal. The presence or absence of the analyte particle (optionally, in certain assay formats, with another optical reporter particle) in contact with the optical reporter particle, induces a change in the optical signal. An optical reporter particle bound to analyte particle ("bound optical reporter particle") will emit a different signal than an optical reporter particle not bound to analyte particle ("unbound optical reporter particle").

The term "optical signal", as used herein, alone or in combination, is used to describe a signal that originates from an optical reporter particle. The optical signal may fall in the visible range of the spectrum, or outside the visible range of the spectrum. The signal may be, for example:
  wavelength of light;
  intensity of signal;
  brightness;
  the shape of a signal or spectrum;
  the presence or absence of spectral bands;
  the extinction coefficient of an absorption band;
  the $\lambda_{max}$ of an absorption band;
  the quantum yield of an emission band; or
  the fluorescence anisotropy of an emission band.

In some embodiments, the optical signal of a reporter particle changes on binding of an analyte particle. In some embodiments, the optical signal of a reporter particle remains unchanged on binding of an analyte particle.

The term "pixel", as used herein, alone or in combination, refers to an area on an area detector, for example an image sensor, whose signal can be measured independently from other pixels. Area detectors are commonly divided into a two-dimensional grid of pixels, with the size of each pixel, and the count of pixels in the two directions, determined by the area detector manufacturer.

The term "precision", as used herein, alone or in combination, is used to refer to the estimate of error that is associated with a reported or estimated value. A low precision measurement, observation, or estimation is associated with a high degree of uncertainty about the closeness of this number to the actual value. A high precision measurement, observation, or estimation is associated with a low degree of uncertainty about the closeness of this number to the actual value. Precision can often be quantified by the use of error bars on graphs or ranges for numerical values. For example, an estimated value that is reported as 10.5±0.1 indicates that the true value is very likely between 10.4 and 10.6; with a small but nonzero chance that the true value is outside this range.

The terms "protein," "polypeptide," "peptide," and "oligopeptide" are used interchangeably herein and include any composition that includes two or more amino acids joined together by a peptide bond. It will be appreciated that polypeptides can contain amino acids other than the 20 amino acids commonly referred to as the 20 naturally occurring amino acids. Also, polypeptides can include one or more amino acids, including the terminal amino acids, which are modified by any means known in the art (whether naturally or non-naturally). Examples of polypeptide modifications include e.g., by glycosylation, or other-post-translational modification. Modifications which can be present in polypeptides of the present disclosure, include, but are not limited to: acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "qualitative analysis", as used herein, alone or in combination, is used to describe a method for determining the absence or presence of an analyte particle in a sample. In some embodiments, a qualitative analysis method reports the presence or absence of a single molecule of analyte in a sample. In some embodiments, a qualitative analysis method reports the presence or absence of a single particle of analyte in a sample. In some embodiments, a qualitative analysis method incorrectly reports the absence of analyte in a sample that contains analyte molecules at a level below a certain threshold. In some embodiments, a qualitative analysis method incorrectly reports the absence of analyte in a sample that contains analyte particles at a level below a certain threshold.

The term "quantitative analysis", as used herein, alone or in combination, is used to describe a method for determining the amount of an analyte particle in a sample.

The term "recording device", as used herein, alone or in combination, refers to a device for recording an optical signal. In certain embodiments, the optical signal is converted to an electrical signal. In certain embodiments, the recording device is a charge-coupled ("CCD") device. In certain embodiments, the recording device is a complementary metal-oxide semiconductor ("CMOS") device.

The term "reporter particle", as used herein, alone or in combination, is used to describe a molecule, supramolecular particle, or nanoscale particle that will bind to an analyte particle of interest and, upon binding of analyte, form aggregates comprising a plurality of reporter particles.

The term "reporter" can refer to a type of substance composed of reporter particles. The term "reporter" can also refer to an amount or concentration of reporter particles. In certain usages, as will be evident from the context, the term "reporter" can refer to a single reporter particle.

The term "reporter volume", as used herein, alone or in combination, is used to describe the volume of the measurement device in which the reporter particles are located. The reporter volume may be substantially the same as the sample compartment, or the reporter volume may be smaller. In certain embodiments, the dimension of the reporter volume that is parallel to the optical paths for the reporter particles will be small. In certain embodiments, the reporter volume will constitute a monolayer.

The term "sample", as used herein, alone or in combination, is used to describe a composition that contains the analyte particle of interest. A sample will often be in fluid, e.g. aqueous, solution. A sample may be chemical or biological. Blood, plasma, water from a source to be tested, extracts from plant, animal, or human tissue samples, are examples of biological samples. A chemical sample would be one that did not contain material of biological origin, such as a water sample containing petrochemical or industrial waste. Biological samples drawn from an organism can include, but are not limited to, the following: blood, serum, plasma, urine, mucus, saliva, sputum, stool, and other physiological secretions, as well as extracts of tissues, and or any other constituents of the body which can contain the target particle of interest. Other similar specimens such as cell or tissue culture or culture broth are also of interest.

A biological sample may be fresh or stored (e.g. blood or blood fraction stored in a blood bank). The biological sample may be a bodily fluid expressly obtained for the assays of this invention or a bodily fluid obtained for another purpose which can be sub-sampled for the assays of this invention. In one embodiment, the biological sample is whole blood. Whole blood may be obtained from the subject using standard clinical procedures. In another embodiment, the biological sample is plasma. Plasma may be obtained from whole blood samples by centrifugation of anti-coagulated blood. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum. In another embodiment, the sample is urine. The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions at physiological pH, such as phosphate, Tris, or the like, can be used.

The term "saturation", as used herein, in reference to binding phenomena, refers to a state in which nearly all reporter particles are bound to analyte particles. A characteristic of a condition of saturation is that an increase in the concentration of analyte particle causes a small increase in the degree of binding of reporter particles.

The term "smartphone" as used herein, refers to a handheld personal computer with a mobile operating system and an integrated mobile broadband cellular network connection for voice, SMS, and internet data communication, and, typically, wi-fi.

The term "tablet computer" or "tablet, as used herein, refers to a thin, flat, portable personal computer, typically with a mobile operating system, LCD touchscreen display, a rechargeable battery, and a wireless (optionally, cellular) communication interface.

Aggregate Formation

In order to promote aggregate formation, the reporter particles comprise a plurality of binding sites, each of which can recognize and bind to one of a plurality of binding sites on the analyte particle of interest. Since both the reporter particle and the analyte contain multiple binding sites, both can bind to more multiple binding partners simultaneously, enabling the formation of polynuclear aggregates. The requirements for this design are that (a) a single analyte particle can bind to two or more reporter particles simultaneously, and (b) a single reporter particle can bind to two or more analyte particles simultaneously.

The principle of this detection system is illustrated in FIGS. 1(a)-(d). An analyte particle of interest contains two identical binding sites, represented schematically in FIG. 1(a) as an oval attached to 2 triangles. The analyte particle is exposed to 2 reporter particles, drawn above the reaction arrow, each of which each contain a triangular binding site. The analyte particle and the 2 reporter particles combine to form a supramolecular ternary 1:2 analyte particle : reporter particle complex. Importantly, the 2 reporter particles are brought into proximity by the formation of the supramolecular aggregate. FIG. 1(b) shows a similar system, with the differences being that the analyte particle has two different binding sites (the triangle and the rectangle), and the medium contains two types of reporter particles (containing a triangular and rectangular binding site).

FIG. 1(c) elaborates on the system of FIG. 1(a) in that the system contains a reporter particle with two identical (triangular) binding sites, each of which can bind to a binding site in the analyte particle. The product of the reaction contains two reporter particles and two analyte particles; however, due to the presence of free binding sites on both reporter particle and analyte particle, additional reporter particles and analyte particles can further bind to the supramolecular structure.

FIG. 1(d) builds on the system of FIG. 1(b) in that the system contains a reporter particle with two different (triangular and rectangular) binding sites, each of which can bind to a binding site in the analyte particle. As with the system in FIG. 1(c), the disclosed product contains two reporter particles and two analyte particles; additional reporter particles and analyte particles can further bind to the supramolecular structure.

Figure 2:
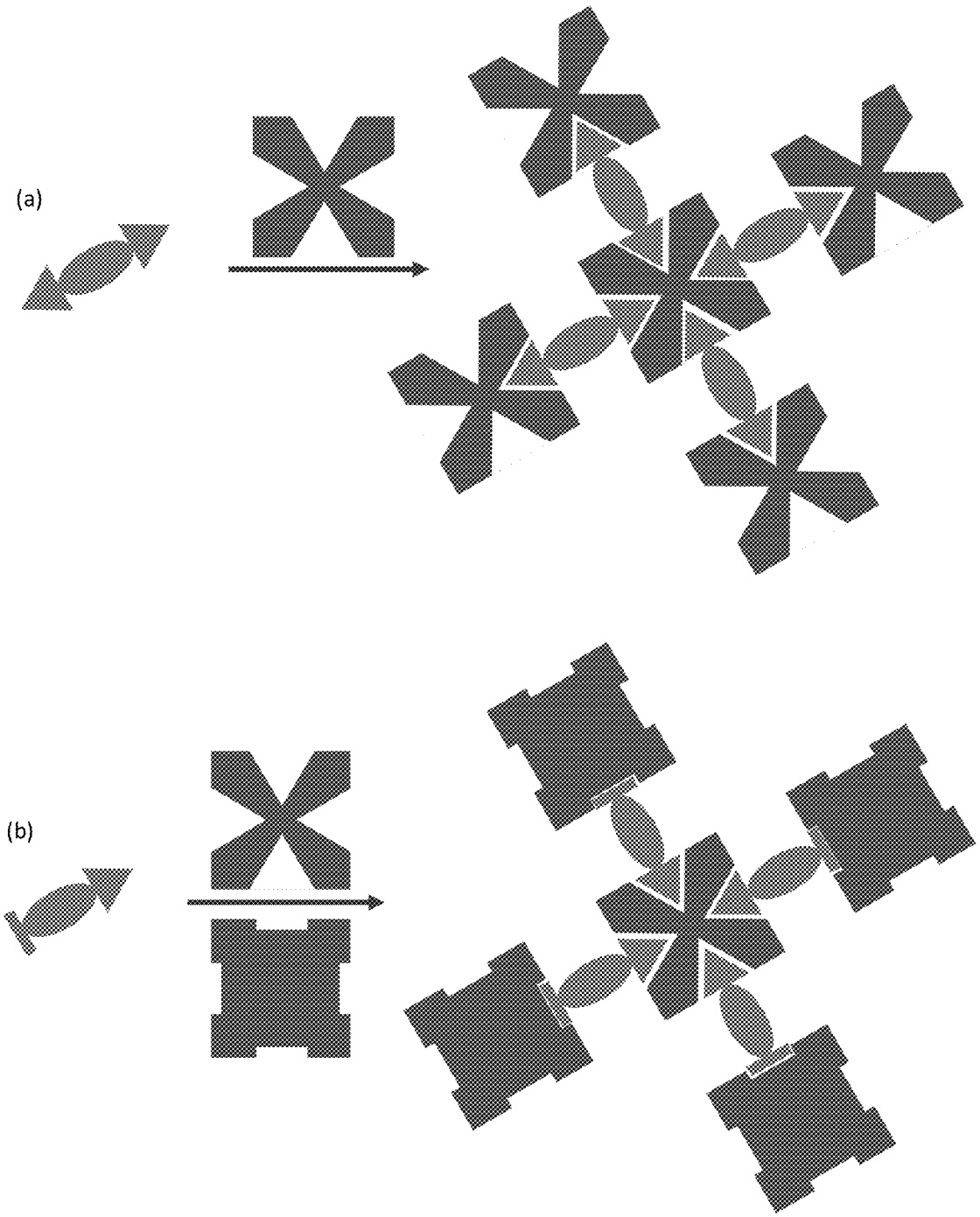
FIG. 2 shows the design principle for reporter particles with 4 binding sites.
Figure 3:
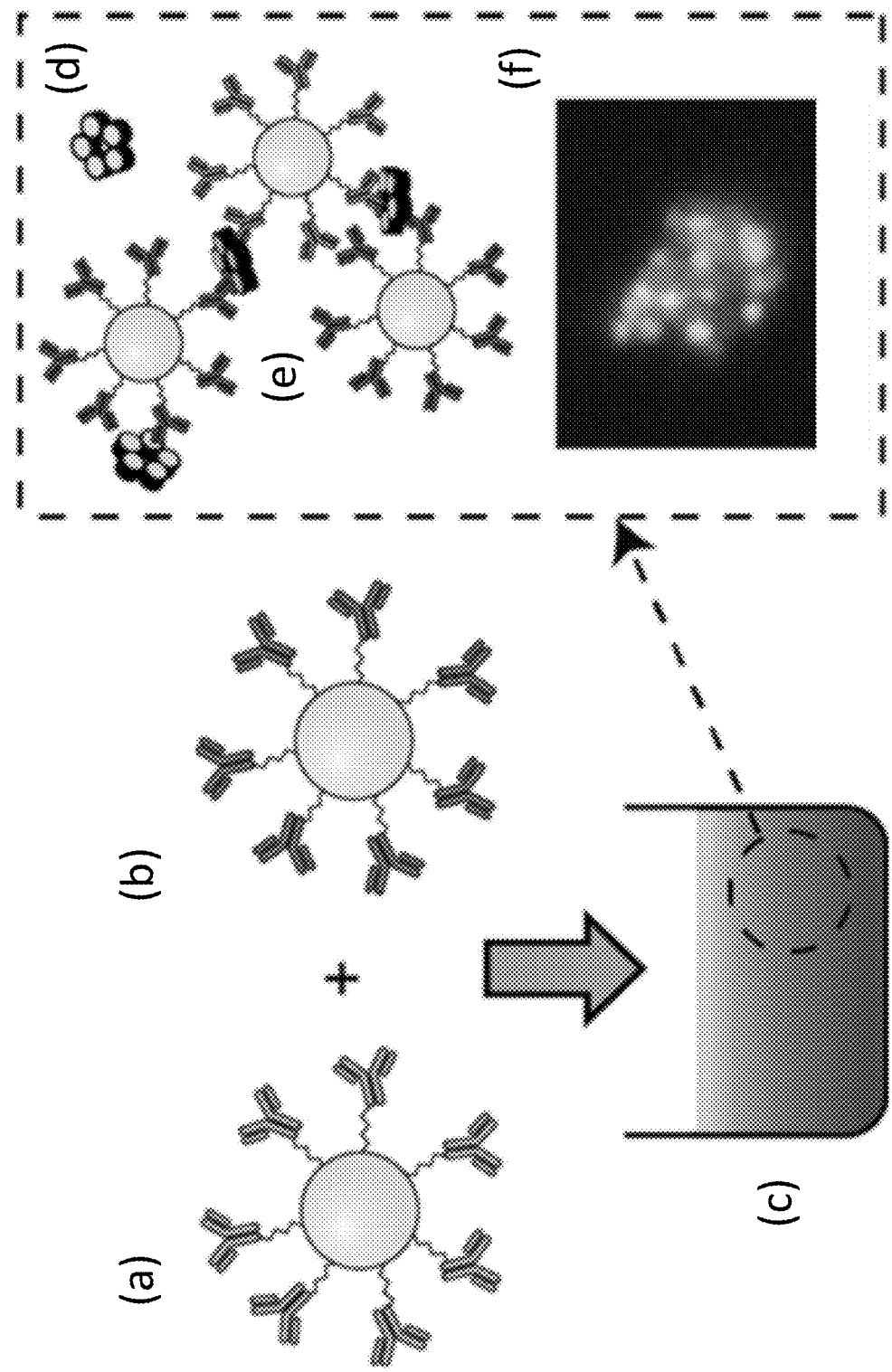
FIG. 3 shows the detection of antigens using gold nanoparticles conjugated to C2 and C6 antibodies.
Figure 4:
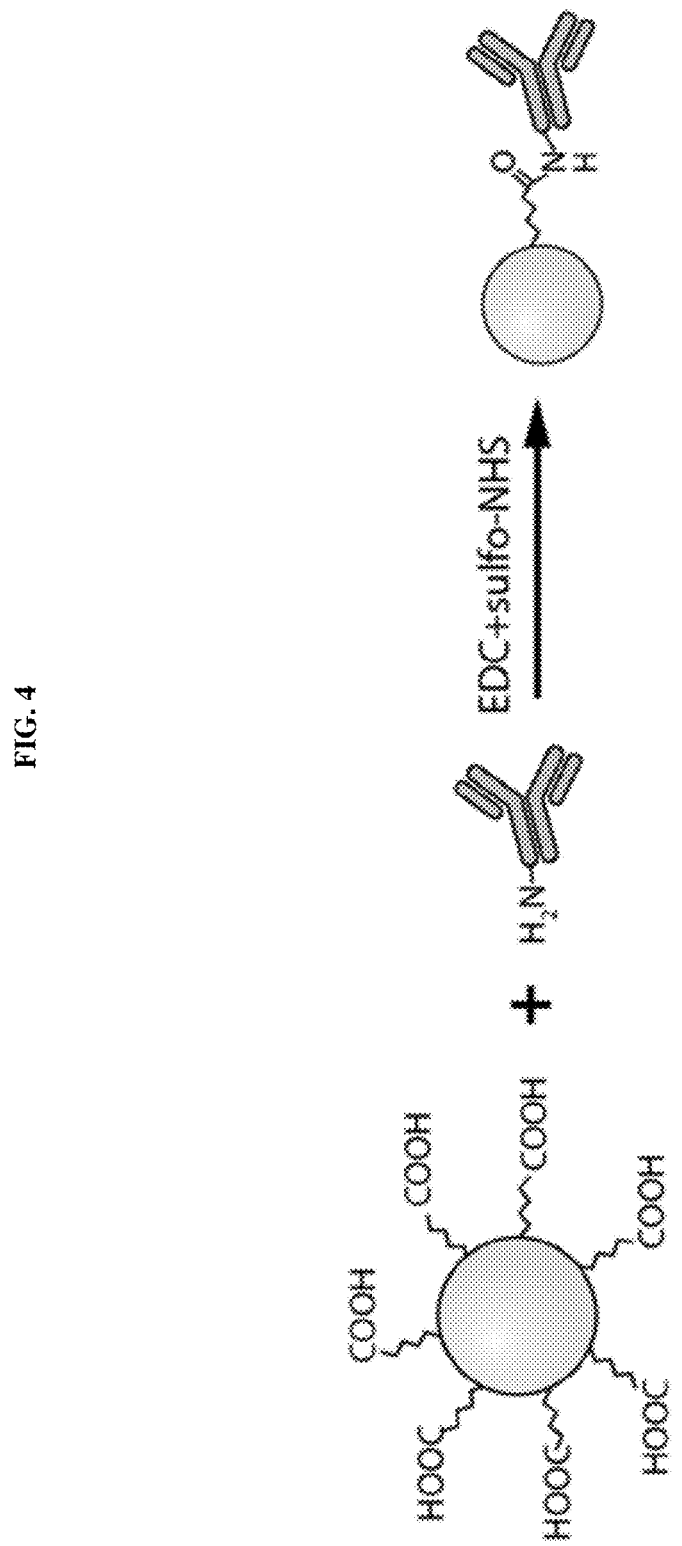
FIG. 4 shows the procedure for conjugation of citrate-capped gold nanoparticles to antibodies.

Elaboration of the design principle is shown in FIGS. 2(a)-(b), with reporter particles that have each four binding sites, and which are intended to bind to analyte particles with two binding sites. Shown in FIG. 2(a) is a reporter particle with this design that is bound simultaneously to four analyte particles, each having two identical binding sites. Each of the analyte particles, in turn, is bound to an additional reporter particle. It will be apparent that each of these four additional reporter particles can, in turn, bind to three additional analyte particles, to form an assembly with a total of 5 reporter particles and 8 analyte particles. This process, not shown for compactness, can be further expanded by the binding of further analyte particles.

The principle can be expanded by introduction of a second reporter particle with a different binding site. Shown in FIG. 2(b) is a pair of nonidentical reporter particles, with different binding sites, intended for binding analyte particles with two different binding sites. The assembly shown on the right is nucleated by the formation of a 1 : 4 aggregate of the first reporter particle with 4 analyte particles, each bonded at one of the two binding sites. Each of the analyte particles, in turn, is bound to one of the second type of reporter particles. As before, each of these four additional reporter particles can, in turn, bind to three additional analyte particles, to form an assembly with a total of 5 reporter particles (one of the first type and four of the second type) and 8 analyte particles. This process can also further expanded by the binding of further analyte particles.

The presence of analyte particles promotes the assembly of an aggregate containing several reporter particles. Assuming, for sake of simplicity, that the chromophores on the reporter particles do not interact with each other, the response of multiple reporter particles in a single aggregate will be additive, i.e., two reporter particles in an assembly will provide twice the spectral signal of a single reporter particle. Additionally, for the purposes of the disclosure, an assembly containing two or more reporter particles will necessarily be twice the size, or more, of a single reporter particle.

Binding phenomena of simpler systems, in which the reporter particle and the analyte particle each have a single binding site, and for which only 1:1 complexes can be formed, has been studied and modelled extensively in chemistry and biochemistry. The degree of binding between the two particles, and formation of 1:1 complexes, is governed by the strength of the intermolecular interaction. Given a fixed concentration of total reporter particles, the concentration of unbound reporter particles asymptotically approaches zero as the concentration of analyte particle is increased.

If either the reporter particle or the analyte particle contain multiple binding sites, complexes with greater than 1:1 stoichiometry can be formed. Assuming that the multiple binding sites operate independently, mathematical modelling of the binding behavior is still manageable. For example, a reporter with 3 equivalent binding sites can form 1:1, 1:2, and 1:3 reporter : analyte complexes. Furthermore, at conditions under which 90% of all reporter binding sites are occupied by an analyte particle (and 10% of all reporter binding site are unoccupied by analyte particle) 99% of reporter particles will bind to at least one analyte. From the fractional occupancy of each reporter binding site, the proportion of each species (i.e., free reporter particle, and the 1:1, 1:2 and 1:3 complexes) can be estimated by statistics.

If both the reporter particle and the analyte particle contain multiple binding sites, mathematical prediction of the proportion of each possible complex will become more cumbersome and less accurate. Binding behavior can be predicted by resorting to certain simplifications and assumptions; more realistically, calibrations curve can be constructed from analysis of solutions of known analyte particle concentrations. These calibration curves can be obtained either for prototype devices, or for individual devices in the field. Furthermore, in certain embodiments, calibration curves can be re-determined after repeated use of the device, or after an extended service time, particularly when the reporter particles degrade over time.

Reporter Particles

The measurement devices and systems comprise, and the methods disclosed herein employ, reporter particles. The requirements for a reporter particle are: (a) a plurality of binding sites for binding to a plurality of analyte particles, (b) capability to provide an optical signal, to allow imaging, (c) large enough so that individual reporter particles can be imaged. The term "reporter particle" thus embraces assemblies of atoms that may be larger than encompassed by alternative definitions of "molecule". Reporter particles provide an optical signal in the presence and, optionally, in the absence of analyte particle.

The reporter particles comprise a plurality of binding sites, in order that a single reporter particle can bind to a plurality of analyte particles. In certain embodiments, the reporter particle comprises a plurality of identical binding sites, each of which can bind to one of a plurality of identical binding sites on the analyte particle. In certain embodiments, the reporter particle comprises a plurality of substantially identical binding sites, each of which can bind to one of a plurality of identical or substantially identical binding sites on the analyte particle. In certain embodiments, the reporter particle comprises a plurality of non-identical binding sites, each of which can bind to one of a plurality of identical, substantially identical, or non-identical binding sites on the analyte particle.

The binding sites of the reporter particles can be provided by different types of molecular functionality. Reporter particles can comprise antibodies (or fragment thereof), nucleic acids, proteins, and peptides, any of which may be chemically or biochemically modified, and any of which can provide the binding interaction with analyte particle. Modern immunochemical methods enable the synthesis of reporter particles suitable for the methods of this disclosure. Antibodies can be raised to various analyte particles of interest and, especially for larger analyte particles, different antibodies can be identified that bind to different regions of an analyte particle, and that can simultaneously bind to analyte particle. Alternatively, reporter particles can contain synthetic motifs, such as those designed with host/guest or supramolecular chemistry and/or synthesized with organic chemistry, that can bind to certain analyte particles.

Reporter particles provide an optical signal in the presence and, optionally, in the absence of binding. In some embodiments, the optical signal is provided by ultraviolet-visible ("UV/vis") absorption. In some embodiments, the optical signal is provided by fluorescence or phosphorescence emission. In certain embodiments, the optical signal of the reporter particle is substantially unchanged on binding of one or more analyte particles. In certain embodiments, the optical signal of the reporter particle is substantially unchanged on binding of a single analyte particle, and is changed on binding of multiple analyte particles. In certain embodiments, the optical signal of the reporter particle is changed on binding of one or more analyte particles. In some embodiments, the change in optical signal is a change in extinction coefficient. In some embodiments, the change in optical signal is a change in quantum yield. In some embodiments, the change in optical signal is a change in absorption wavelength. In some embodiments, the change in optical signal is a change in emission wavelength. In some embodiments, the change in optical signal is a change in fluorescence anisotropy.

The reporter particles may comprise a chromophore. In certain embodiments, the chromophore has been covalently attached to the reporter particle; alternatively, it may attach to the reporter particle via functionalization, e.g. to the surface of a quantum dot or plasmon nanoparticle. In certain embodiments, the chromophore absorbs electromagnetic radiation. In certain embodiments, the chromophore absorbs electromagnetic radiation in a spectral region chosen from visible and ultraviolet. Alternatively, the chromophore may scatter electromagnetic radiation. In certain embodiments, the chromophore is luminescent. In certain embodiments, the chromophore is fluorescent. In certain embodiments, the chromophore is phosphorescent.

In some embodiments, reporter particles have sufficient size without further modification so that individual reporter particles can be imaged. In some embodiments, reporter particles can be chimeric particles comprising a moiety of biochemical origin and a synthetic moiety; examples include an antibody-functionalized plasmonic nanoparticle or quantum dot and a nucleotide-functionalized plasmonic nanoparticle or quantum dot. The synthetic moiety can provide the optical signal and/or the size required so that individual reporter particles can be imaged. In some embodiments, the reporter particle comprises a nanoparticle or quantum dot. In some embodiments, the nanoparticle or quantum dot is conjugated to the binding site via a covalent bond. In some embodiments, the nanoparticle or quantum dot is conjugated to the binding site via an ester or amide bond. In some embodiments, the nanoparticle or quantum dot is conjugated to the binding site via a thioether or thiolester bond.

Object Characteristics

The disclosure measures characteristics of the aggregate which can provide information about the degree of aggregation and which, in turn, provides information on the presence, or concentration, of analyte. The term "object characteristic" therefore refers to a property of the aggregate which is related to the size of the aggregate. In some embodiments, the object characteristic is related to the median size of the aggregate. In some embodiments, the object characteristic is related to the mean size of the aggregate. In some embodiments, the object characteristic is related to the RMS size of the aggregate. In some embodiments, the object characteristic is directly proportional to the (median/mean/RMS) size of the aggregate. In some embodiments, the object characteristic is monotonically related to the (median/mean/RMS) size of the aggregate. In some embodiments, the relationship between the object chararcteristic and the (median/mean/RMS) size of the aggregate can be estimated by means of a calibration curve. In some embodiments, the relationship between the object chararcteristic and the (median/mean/RMS) size of the aggregate can be estimated by means of a Newton-Raphson least-squares fitting method. In some embodiments, the object characteristic is chosen from the (median/mean/RMS) size of the aggregate, as directly observed or estimated, the (median/mean/RMS) perimeter of the aggregate, as directly observed or estimated, the shape of the aggregate, the color of the aggregate, the brightness of the aggregate, the reflectivity of the aggregate, the luminescence (fluorescence/phosphorescence) of the aggregate. In some embodiments, the estimation of (median/mean/RMS) particle size is determined from combination of two or more such object characteristics.

Image Processing

In certain embodiments, the frames of the detector volume are evaluated "raw", without any further image processing. In certain embodiments, the frames of the detector volume are filtered to separate noise, error, or background features from genuine particle aggregates. In certain embodiments, the frames of the detector volume are filtered to separate error from genuine particle aggregates. In certain embodiments, the frames of the detector volume are filtered to separate noise from genuine particle aggregates.

Inactive Reporter Particles

The methods described herein accommodate a certain fraction of reporter particles that is inactive, i.e., the optical signal from these inactive reporter particles is either absent or substantially different from the bulk of reporter particles. This behavior can be due to (a) the failure of a reporter particle to bind to the analyte particle, or (b) a reporter particle can bind to the analyte particle but does not produce an optical signal, or produces an optical signal that is substantially different from the remainder of reporter particles.

The presence of inactive reporter particles of both types will pose less of a complication for the aggregation-based assay of the present disclosure than in various other methods. In the first instance, reporter particles which do not bind to the analyte particle will not participate in the aggregate formation process, and will simply remain as individual particles in the assay. In the second instance, the aggregation-based assay does not require that binding of reporter particle with analyte particle perturb the optical signal, since the role of the optical signal is to image the aggregates and estimate their size. For this reason, reporter particles whose optical signal remains unchanged on binding with analyte particle may be preferred. In contrast, many assays that rely on reporter/analyte binding would perform poorly or not at all, in cases for which the change in optical signal is not uniform among reporter particles.

In certain embodiments of the disclosure, an inactive reporter particle comprises individual proteins (including antibodies) that have aggregated, a peptide or protein that has not correctly folded, a peptide or protein that comprises an incorrect residue, a defective chromophore.

The number of inactive reporter particles can remain substantially constant during the operating lifetime of the measurement device, particularly in cases in which inactive reporter particles have defective composition. It is also possible that the number of inactive particles will increase during the operating lifetime of the measurement device, due to chemical deterioration of reporter particles, particularly photochemical deterioration caused by repeated high intensity exposure to light sources, or aggregation of protein forming part of the reporter particle.

Inactive reporter particles can be identified by a change in optical behavior: either their failure to produce an optical signal on exposure to analyte particles, or the their production of an optical signal on exposure to analyte particles that is significantly different from the bulk of the reporter particles.

Signal Processing

In certain embodiments, each of the one or more frames of the detector volume array consist of an array of pixels. Each of the one or more frames can be processed into a digital record, using methods known in the art.

In certain embodiments, the records for the one or more images contain intensity information for each pixel. In some embodiments, the intensity information for each pixel is determined by an analog-to-digital converter ("ADC") which converts intensity information observed at each pixel of the detector to digital form. The dynamic range of intensity information can be correlated to the nature of the ADC: for example, use of a 12-bit ADC provides, for each pixel, an intensity value ranging from 0 to $(2^{12}-1)$, or 0 to 4095. In some embodiments, a color signal is obtained. In some embodiments, the color signal is converted to grayscale. In some embodiments, a grayscale signal is obtained.

Processing of the computer records can include the step of removing spurious noise. In certain embodiments, features in the computer records that are smaller than a user-supplied threshold are considered noise and are removed from processing. In certain embodiments, features in the computer records that are larger than a user-supplied threshold are considered noise and are removed from processing. In certain embodiments, features in the computer records that are less intense than a user-supplied threshold are considered noise and are removed from processing.

Processing of the computer records can include the step of identifying features in the images that correspond to aggregates. The computer can identify boundaries between features and background. These boundaries can be identified in the frames by locating regions in the frame with large light-to-dark gradients corresponding to transitions between (bright) aggregates and (dark) backgrounds.

Processing of the computer records can include the step of calculating the area of each feature on the frame. The processing can further include the step of calculating the size of each aggregate that corresponds to each feature on the frame.

Processing of the computer records can also include the step of analyzing information on the size of each aggregate, and from this analysis the concentration of analyte can be estimated. In some embodiments, the analysis can be based on binding isotherm properties of the reporter particle/analyte particle pair. In some embodiments, the analysis can be based on comparison with controls with predetermined quantities of reporter particle and analyte particle. In some embodiments, the comparison can be made using the mean aggregate size in solution. In some embodiments, the comparison can be made using the entirety of the observed aggregate size distribution. In some embodiments, the comparison is performed with a least squares fit. In some embodiments, the least squares fit is weighted by the estimated error of each particle size estimation.

Figure 20:
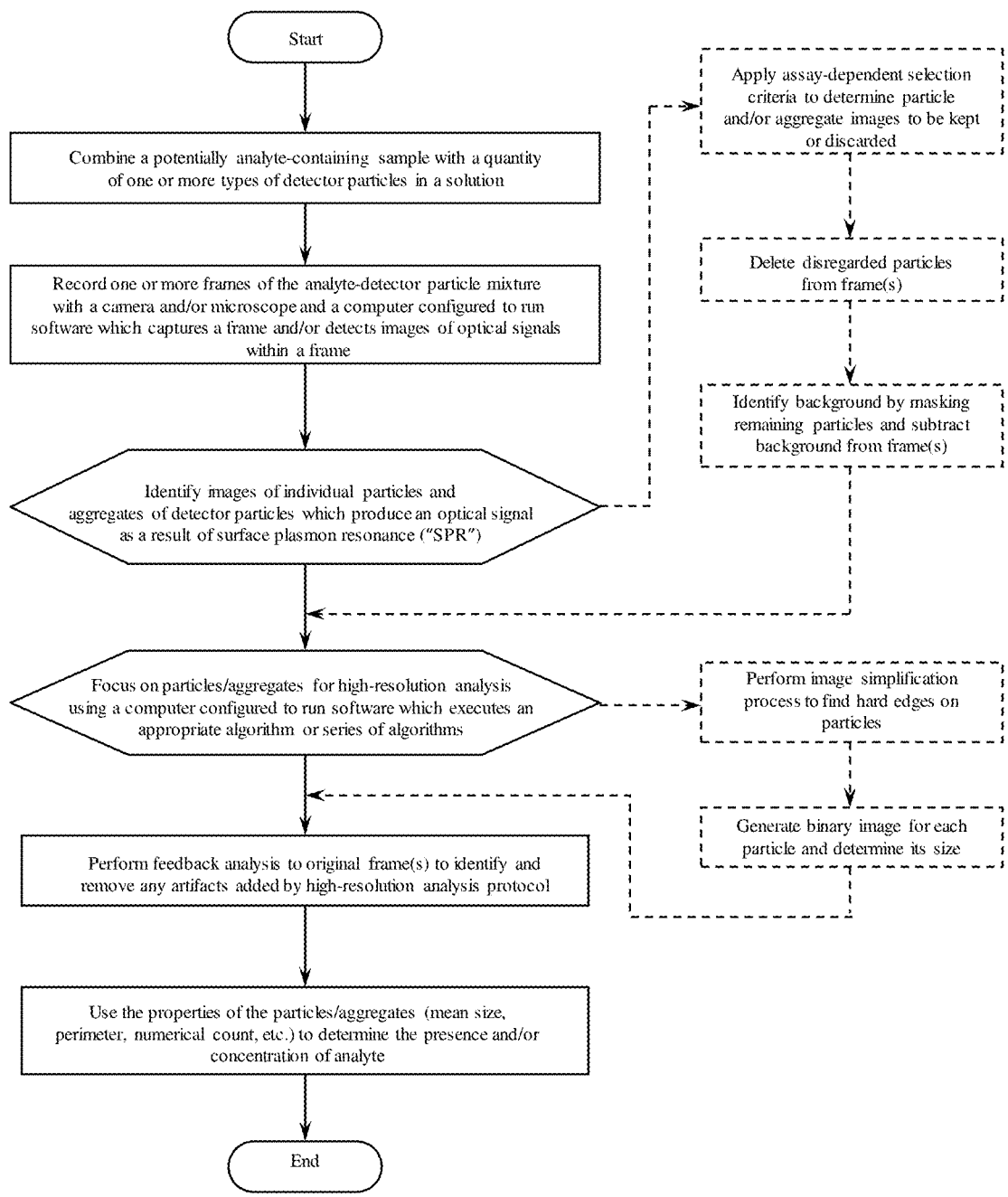
FIG. 20 shows a flow chart for processing of images.

A flow chart for performance of the analysis is provided in FIG. 20. Briefly, a sample is incubated with detector particles in solution, after which time frames are recorded of the solution. Images for individual particles and aggregates are identified. Selection criteria, dependent on the particular assay, can be used to keep or discard individual images. Background subtraction is accomplished by masking the selected images and subtracting the resulting pixels from the overall frame. Individual images that are particularly suitable for analysis are then selected, and hard edges are generated using established algorithms. Particle size is then estimated from the binary image. Feedback analysis is then applied to the original frame(s) in order to identify and remove any artifacts. From the properties determined from the set of selected and quantified images (mean size, perimeter, count, etc.), analyte presence and/or concentration can be determined.

Applications

The aggregation assay methods, systems, and devices disclosed herein are useful in a variety of fields and applications. In particular, aggregation assays would be useful in "the field," that is, in a portable setting. For example, aggregation assays would be useful in medical assessment and diagnostics and detection of pathogens, particularly in remote areas, areas that are underserved or difficult to access (e.g. due to violent conflict), areas affected by an epidemic, and in other instances where access to traditional assay equipment and/or professionals is limited. They would also be useful within a hospital or clinic, or in a home-visit setting, where they could be performed or used at point of care or bedside.

Aggregation assays would be equally useful in a veterinary setting as in a medical, whether in a veterinary office, on a ranch or farm, or anywhere animals in need of testing are located. They could also be used in horticultural or agricultural applications to test plants or soil for pathogens or symbiotic microorganisms, or detect other genotypes and phenotypes of interest.

Aggregation assays could also be used to test water for contamination, e.g., by bacteria, algae, or fungi, or the toxic products thereof; by petroleum or its products and by-products, and industrial waste). Such assays would be useful for food safety testing and for agricultural uses, such as field or processing facility testing for pathogens, toxins, adulterants, contaminants, and pests.

Assays

Many types of biochemical assays are adaptable to the aggregation assay format disclosed herein. Examples include: immunoassays in which capture and binding of an antigen by an antibody or a fragment thereof; hybridization assays in which one or more segments of DNA or RNA complementary to analyte particle DNA/RNA of interest is used to capture the analyte particle; and ligand binding assays in which a binding partner to a receptor, enzyme, or other protein, or vice versa, is used as the capture agent for the partner analyte particle (e.g., protein or fragment thereof).

In some embodiments, a heterogeneous assay protocol is used which utilizes more than one type of reporter particle. The presence of multiple types of reporter particles may simplify issues of synthesis and aggregation. Furthermore, since the method images entire aggregates, comprising multiple reporter particles, only a single type of reporter particle need to provide an optical signal in order to provide an image of the aggregate.

The methods disclosed herein can be used to identify a phenotypic or genotypic state of interest associated with a clinically diagnosed disease state. Such disease states include, for example, cancer, cardiovascular disease, inflammatory disease, autoimmune disease, neurological disease, infectious disease and pregnancy related disorders. Alternatively, states of health can be detected using markers.

Cancer phenotypes are included in some aspects of the invention. Examples of cancer herein include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell hung carcinoma gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyoma tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforme, leukemias, lymphomas, malignant melanomas, epidermoid carcinomas, and other carcinomas and sarcomas.

Cardiovascular disease can be included in other applications of the invention. Examples of cardiovascular disease include, but are not limited to, congestive heart failure, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, myocardial ischemia, myocardial infarction, cardiac tamponade, myocarditis, pericarditis, arrhythmogenic right ventricular dysplasia, hypertrophic cardiomyopathy, Williams syndrome, heart valve diseases, endocarditis, bacterial disease, pulmonary atresia, aortic valve stenosis, Raynaud's disease, cholesterol embolism, Wallenberg syndrome, Hippel-Lindau disease, and telangiectasias.

Inflammatory disease and autoimmune disease can be included in other embodiments of the invention. Examples of inflammatory disease and autoimmune disease include, but are not limited to, rheumatoid arthritis, non-specific arthritis, inflammatory disease of the larynx, inflammatory bowel disorder, psoriasis, hypothyroidism (e.g., Hashimoto thyroidism), colitis, Type 1 diabetes, pelvic inflammatory disease, inflammatory disease of the central nervous system, temporal arteritis, polymyalgia rheumatica, ankylosing spondylitis, polyarteritis nodosa, Reiter's syndrome, scleroderma, systemic lupus and erythematosus.

The compositions and methods disclosed herein will be useful for the detection of viruses. As is shown elsewhere, viruses comprise surface macromolecules, generally proteins, that are responsible for invasion of the virus into a cell. These surface macromolecules comprise recognition elements that interact with corresponding features on the invaded cell. Well-known examples of these surface macromolecules are the spike proteins of coronaviruses. These surface molecules can be exploited as binding sites for suitably functionalized reporter particles.

The methods and compositions of the invention can also provide laboratory information about markers of infectious disease including markers of Adenovirus, Bordetella pertussis, Chlamydia pneumonia, Chlamydia trachomatis, Cholera Toxin, Cholera Toxin β, Campylobacter jejuni, Cytomegalovirus, Diphtheria Toxin, Epstein-Barr NA, Epstein-Barr EA, Epstein-Barr VCA, Helicobacter Pylori, Hepatitis B virus (HBV) Core, Hepatitis B virus (HBV) Envelope, Hepatitis B virus (HBV) Surface (Ay), Hepatitis C virus (HCV) Core, Hepatitis C virus (HCV) NS3, Hepatitis C virus (HCV) NS4, Hepatitis C virus (HCV) NS5, Hepatitis A, Hepatitis D, Hepatitis E virus (HEV) orf2 3 KD, Hepatitis E virus (HEV) orf2 6KD, Hepatitis E virus (HEV) orf3 3 KD, Human immunodeficiency virus (HIV)-1 p24, Human immunodeficiency virus (HIV)-1 gp41, Human immunodeficiency virus (HIV)-1 gp120, Human papilloma virus (HPV), Herpes simplex virus HSV-1/2, Herpes simplex virus HSV-1 gD, Herpes simplex virus HSV-2 gG, Human T-cell leukemia virus (HTLV)-1/2, Influenza A, Influenza A H3N2, Influenza B, Leishmania donovani, Lyme disease, Mumps, M. pneumoniae, M. tuberculosis, Parainfluenza 1, Parainfluenza 2, Parainfluenza 3, Polio Virus, Respiratory syncytial virus (RSV), Rubella, Rubeola, Streptolysin O, Tetanus Toxin, T. pallidum 15 kd, T. pallidum p47, T. cruzi, Toxoplasma, and Varicella Zoster.

It will also be appreciated that the same recognition features that enable aggregation-based detection of viruses can be applied to larger organisms, such as archaea, bacteria, and other microorganisms. For example, bacteria often comprise glycoproteins on the surface that can be utilized as recognition sites.

The methods disclosed herein can be used to detect genetic variation. The genetic variation herein may include, but is not limited to, one or more substitution, inversion, insertion, deletion, or mutation in nucleotide sequences (e.g., DNA and RNA) and proteins (e.g., peptide and protein), one or more microdeletion, one or more rare allele, polymorphism, single nucleotide polymorphism (SNP), large-scale genetic polymorphism, such as inversions and translocations, differences in the abundance and/or copy number (e.g., copy number variants, CNVs) of one or more nucleotide molecules (e.g., DNA), trisomy, monosomy, and genomic rearrangements. In some embodiments, the genetic variation may be related to metastasis, presence, absence, and/or risk of a disease, such as cancer, pharmacokinetic variability, drug toxicity, adverse events, recurrence, and/or presence, absence, or risk of organ transplant rejection in the subject. For example, copy number changes in the HER2 gene affect whether a breast cancer patient will respond to Herceptin treatment or not. Similarly, detecting an increase in copy number of chromosome 21 (or 18, or 13, or sex chromosomes) in blood from a pregnant woman may be used to as a non-invasive diagnostic for Down's Syndrome (or Patau's Syndrome or Edwards' Syndrome) in an unborn child. An additional example is the detection of alleles from a transplanted organ that are not present in the recipient genome-monitoring the frequency, or copy number, of these alleles may identify signs of potential organ rejection.

Measurement Devices and Systems

The aggregation assay methods described herein employ a measurement device or system, either of which comprises the parts required for analysis of samples. The measurement device contains a sample compartment, into which samples are introduced, either by direct addition of the sample of interest, or by insertion of a cuvette or slide, which itself contains the sample of interest. The sample compartment further provides a component that contains reporter particles, whose function is to bind to the analyte particle of interest and form aggregates. For designs which rely on emission methods, the measurement device provides an illumination device for excitation of chromophores contained in the reporter particles. The measurement device contains a recording device (e.g. an image sensor, e.g. a digital camera), which detects and records the optical signal from the reporter particles. Finally, the measurement device can contain additional components, such as controls for operation, a device for displaying or reporting analysis results, and an interface with an external computer. The presence of the various optional components, and their specifics, may differ among various designs of measurement devices.

The system or device as a whole can incorporate a mount for orienting the device for convenient sample addition or removal. The system can be coupled to a mobile computing device. The mobile computing device could be a smartphone, handheld computer, tablet computer, or a similar portable computing device. In some examples, the mobile computing device includes all necessary components, such as: display, a processor, a memory, and program instructions stored in the memory and executable by the processor, to enable highly automated performance of steps such as: (i) introduction of sample, (ii) optical excitation, (iii) optional pre-screening of the sample to evaluate sample quality and optimal exposure time, recording of a frame by the recording device, (iv) subtraction of detector bias, if required, (v) digitization of detector signal, (vi) recording of digital signal in nonvolatile memory, (vii) recycling of detector, if needed, and (viii) processing of digital signal. The functions could further include determining the result of the aggregation assay, and conveying the result in visual form to the end user.

The use of a smartphone or other mobile computing device as the detection instrument for aggregation assays allows inexpensive, portable, and multifunctional systems to perform assays in the field, i.e., outside the laboratory. Applications can include point-of-care diagnostic systems for measuring viral loads, nutritional status, disease biomarkers, or environmental contaminants without the need to transport a sample to a central laboratory. Such tests could be performed in private residences, global-health facilities, in law enforcement installations, and medical clinics. The mobile computing device can connect to the internet, which will enable combination of sensor data with patient information and geographical location. Connectivity to an external computation facility can be provided for data interpretation, geographic and demographic mapping, database construction and maintenance, and delivery of notifications to remote medical experts and authorities. Compact, field-operable digital measurement devices will free assays from the requirements for trained technicians in laboratories. Instead, these assays could be performed by anyone, due to the size and affordability of the detection system.

Sample Compartment

The measurement device provides a sample compartment suitable for introduction of a sample of interest. Measurement devices that employ optical measurement techniques will benefit from a sample compartment that is oblong, with one short dimension. The light path for the optical signal from the reporter particles to the recording device will align parallel with the short dimension. This orientation will minimize absorption and dispersion of the optical signal that would cause problems for longer optical paths. This criterion allows for the use of either prismatic or cylindrical sample compartments.

Reporter Volume

The sample compartment comprises a component, termed the reporter volume, that contains reporter particles. This component obviates the need to add reporter particles to the sample of interest, and will instead enable recycling of the reporter particles. In some embodiments, the reporter volume is defined by a physical enclosure that retains reporter particles within itself. The physical enclosure may be porous, to allow passage of analyte particle into the reporter volume for contact with the reporter particle. In some embodiments, the reporter volume is not defined by a physical enclosure; instead, other means can be provided to retain reporter particles within the reporter volume.

The degree to which optical paths overlap can be estimated from a small number of parameters that define the receptor volume, including the particular distribution of reporter particles (random, semi-random, aggregated, ordered), the concentration and effective size of the reporter particles, and the thickness of the reporter volume. In certain embodiments of the disclosure, substantially all optical paths between reporter particles and the recording device encounter no other reporter particle. In certain embodiments, substantially all optical paths between reporter particles and the recording device encounter at most one other reporter particle.

In some embodiments, the reporter volume is sufficiently thin so as to allow for a single layer for the reporter particles. In this design, overlap of optical paths is not possible, since all reporter particles are substantially in a plane perpendicular to the optical path, and parallel to the recording device.

Recording Device and Microscope

A recording device is provided to record the optical signal from the reporter particles. In certain embodiments, the optical signal from the reporter particles passes through a transparent window of the sample compartment. In certain embodiments, the recording device will be an image sensor, such as a camera. A CMOS (complementary metal-oxide semiconductor) camera, for example, is useful because it can read each pixel individually; additionally, CMOS cameras consume very little power, allowing them to last longer when used as part of a device in the field. Almost all smartphone cameras have CMOS cameras, many with resolution of over 10 megapixels, making them useful in the methods, systems, and devices disclosed herein.

In certain embodiments of the disclosure, the recording device allows the observation of one or more signals from the sample compartment. In certain embodiments, each of a plurality of signals originates from a different region of the sample compartment. In certain embodiments, each signal in the plurality of signals originates from a pixel in a regular geometric grid that spans the sample compartment.

In certain embodiments, the pixels of a recording device are arranged in a rectangular or square array. In certain embodiments, the pixels of a recording device are arranged in a 512×512 square array, a 1024×1024 square array, a 2048×2048 square array, or a 4096×4096 square array. In certain embodiments, the signal from each pixel is recorded separately from all other pixels. In certain embodiments, the signal from 2×2 sets of pixels is binned together.

The measurement device can allow the observation of a plurality of signals from different regions of the plurality of reporter particles. In certain further embodiments, the different regions of the plurality of reporter particles are disposed in a regular grid. Alternatively, the individual optical signal from substantially all reporter particles can be observed without interference from any other reporter particle.

Used in combination with a magnifying lens, the recording device can detect even smaller signals. Such lenses are well known in the art. In certain embodiments, the recording device can capture individual pixels and/or individual reporter particles. The use of plasmon nanoparticles/quantum dots as substrates to which capture elements are functionalized facilitates this detection.

The recording device can use any technique that is known in the art for detection and quantification of reporter particle/analyte particle complexes. Recording devices can use optical absorption and emission methods that are paired with the reporter particle design.

Alternatively, the optical output can include fluorescence emission from fluorophore either on the reporter particle or coupled with the reporter particle that is excited by a light source. The presence and quantity of analyte particle would then be reported by the intensity of the fluorescence emission. The fluorophore could be proximal to a surface, such as a photonic crystal, such that the fluorescence emission is enhanced. Multiple fluorophores can be employed to tune the fluorescence signal to a desirable outcome. Thus, the optical signal can be modulated by excitation transfer among two or more fluorophores.

Fluorescence and phosphorescence quantum yield, $\lambda_{max}$ shift, and anisotropy are envisioned in this disclosure. For anisotropy measurements, polarizers can be introduced into either the excitation or emission optical pathway, or both. A light source can be coupled with the emission methods. The light source can be a conventional broadband source, light emitting diode, or laser, and can be delivered to the sample either directly or via a wavelength selection device such as a grating, in order to optimize excitation. Light can be directed through a total internal reflection component incorporating a waveguide and forming the base of the base of the reporter volume, thus providing dark field excitation.

Identification of Inactive Reporter Particles

Provided herein are methods for identifying inactive reporter particles, termed "identification method". For certain systems, two solutions, the first free of analyte particle, and the second with a high concentration of analyte particle, will be submitted sequentially with the reporter volume. It will be appreciated that these two solutions will cause an absence of analyte particle binding by reporter particle, and near saturation of analyte particle binding by reporter particle, respectively. Frames are recorded using the recording device, and a comparison is made between the frames for the analyte particle-free and analyte particle-saturated conditions. Reporter particles that do not meet selectivity criteria are marked as inactive.

In the case of inactivation due to nanoparticle aggregation, identification of inactive reporter particles will be straightforward. Formation of aggregates will be apparent on visual inspection of the frames from the recording device, and will not require the "analyte particle-free" and "analyte particle-saturated" procedure outlined above.

The identification method maintains a record for the location of reporter particles in the measurement device. The location of reporter particles can be referenced by x/y coordinates, for example, relative to an appropriate geometric grid in the measurement device, or relative to the pixel coordinates on the recorder device. The record of inactive reporter particles can be maintained on non-volatile computer memory.

The identification method will provide criteria for tagging reporter particles as inactive. The criteria are set to strike a balance between eliminating poorly behaving reporter particles from use, while maintaining a sufficiently high count of reporter particles for the particular accuracy and sensitivity requirements for the measurement device. In order to eliminate bias, and enable automated tagging, a numerical threshold can be chosen, based on the type of optical signal that is observed. By way of example only, a certain reporter particle may undergo a shift in emission $\lambda_{max}$ on binding to an analyte particle, and the $\lambda_{max}$ shifts by 20 nanometers (nm) for the bulk of the compounds in this example. A threshold of a 5 nm shift might be chosen for this particular example.

In order to satisfy requirements for accuracy and sensitivity, the numerical threshold can be chosen in order to exclude a certain fraction of reporter particles. Referring to the previous example, a $\lambda_{max}$ shift of 12 nm may be observed for 95% of the reporter particles. A threshold $\lambda_{max}$ of 12 nm may then be chosen in order to retain 95% of the reporter particles as active, and discard 5% of the reporter particles as inactive.

A variety of criteria can be applied for assigning an inactive status. Importantly, any criteria can be chosen for assigning reporter particles as inactive. Since the binding of any one reporter particle is independent of all other reporter particles, elimination of a reporter particle from the pool of active reporter particles does not affect the behavior of the remaining particles.

If indicated, the identification method described above can be repeated periodically during the operating lifetime of a measurement device. This practice will be particularly beneficial for reporter devices whose performance is susceptible to deterioration over time. Ideally, the identification method will require a minimal amount of operator intervention, with the measurement device automatically performing all required steps. For the case of nanoparticle-based reporter particles, frames can be recorded periodically, and any aggregation that may occur over time can be identified by pattern-matching software.

The identification method can also comprise the steps of subjecting the measurement device to one or more solutions containing intermediate concentrations of analyte particle. This will be particularly important for quantitative measurement of analyte particle, for which a range of reporter particle saturation is envisioned. By use of several solutions, spanning a range of analyte particle concentrations, a calibration curve can be constructed to better match optical reporting data with concentration of analyte particle.

A key benefit from the use of spatially resolved signals from a field of reporter particles is that regions of the recording device that are particularly problematic can be flagged as such, and discarded in subsequent analyses. This includes not only cases for inactive reporter particles, i.e., improperly folded antibodies, but for any region that presents difficulties. This may include overlapping spots from two or more closely spaced reporter particles, or reporter particles whose free and bound states are poorly distinguishable, for whatever reason. Binding of each individual reporter particle is independent of all others, and discarding a small set of optical signals can improve accuracy or precision, while impacting sensitivity only marginally.

Accuracy/Precision/Sensitivity

It is expected that accuracy for the disclosed digital measurement methods will be at least as good as for conventional analog methods. The digital measurement methods will minimize or eliminate several sources of error, which by definition is the source of low accuracy. By way of example, a potential of error arises from reporter particles which are inactive: either they do not bind to the analyte particle, or bind to the analyte particle and do not provide the expected optical signal. As discussed elsewhere, the presence of reporter particles that do not bind to analyte particle simply represents a fraction of reporter particles that do not form aggregates, and can be taken into account by calibration against samples of known concentration of analyte. Furthermore, since the aggregation assay design does not require that the optical signal be perturbed on binding of analyte, reporter particles can be employed whose chromophores are relatively insensitive to binding of guest. For both of these reasons, inactive particles pose far less of a challenge to accuracy and precision than for many other host/guest based analytical systems.

It is expected that precision for the disclosed digital measurement methods will be at least as good as for conventional analog measurements. Conventional methods, which observe a bulk signal from the entirety of reporter particles, can provide precision estimates using various statistical and numerical methods in most, but not all cases.

In contrast, using the aggregation assay, particularly for systems and conditions which lead to relatively small aggregate formation, the assay can be considered "digital" in that only a small integer number of reporter particles constitute each aggregate. It will be possible to assign an observed particle size (as specified in, e.g. pixel span or physical size in the sample volume) to a "digital" aggregate size, containing an integer count of reporter particles. In some embodiments, it may be preferable that small aggregates are formed intentionally, either due to weak reporter particle/analyte binding, or due to pre-dilution of the sample.

Binding Isotherm

The relation between the concentration of analyte particle on the number and particle size, referred to herein as the "binding isotherm", is complex and indirect. In short, given a fixed reporter particle concentration, the ratio of bound/total binding sites on the reporter particles increases asymptotically to 1 as the concentration of total analyte particle increases. A higher affinity reporter particle will bind to a higher proportion of analyte particle at any given analyte particle concentration. Importantly, the total reporter particle concentration refers only to the active reporter particle.

In many uses that are envisioned for the disclosed methods, thresholds or cutoffs have been established that correspond to critical values. These thresholds or cutoffs can correspond to regulatory levels set by environmental laws, or to critical biomarker levels that correspond to certain health conditions. The measurement methods can adjust the recommended scan parameters and dilution level in order to provide measurement conditions that are adequate for the intended use.

In certain embodiments, the measurement device can provide a mechanism for the automatic dilution of a sample. This can be accomplished by ejecting a fraction of an existing sample, followed by introduction of solute for dilution. This can also be accomplished by introducing a new sample that has been pre-diluted with solute.

In certain embodiments, the recommended dilution level can be calculated by a computing device, either incorporated into the measurement device or connected to the measurement device. The computing device can provide the recommended dilution level to the operator via an interface (such as a display, printout, or synthesized voice report). The computing device can also directly control the measurement device to perform any steps needed to automatically analyze a diluted sample, without the need for user intervention.

In certain embodiments, the thresholds or cutoffs can be pre-set in the computing device, either in the form of firmware, which can be optionally updated in the case a threshold or cutoff changes, or in the form of software. In addition, the operating software can prompt the user for further input on the sample that is being measured. For example, in the case of the measurement of biomarkers, the user can input history parameters for a subject, such as age, weight, gender, and the like, that may alter a threshold or cutoff and that may therefore influence the precision that is required for a given measurement.

As will be demonstrated in the Examples, an important feature of the aggregate assay is that mean particle size can increase smoothly across a range of analyte concentrations. This behavior is due the statistically diminishing unlikelihood of forming larger aggregates, which require multiple simultaneous binding interactions. This behavior stands in contrast to conventional 1:1 binding behavior, which often displays sigmoidal off-on behavior over a narrow range of analyte concentration. Stated differently, the 1:1 binding isotherm leads to a situation in which the reporter particle is either substantially bound or substantially unbound for the overwhelming majority of an analyte concentration range. For this reason, conventional 1:1 binding is of limited value in determine the concentration of an analyte (as opposed to the presence/absence of an analyte). In contrast, the smooth relationship between analyte concentration and particle size lends itself well to precise determination of analyte concentration.

Abbreviations

The following abbreviations are used in this disclosure. Other abbreviations that are recognized by a person of skill in the art may also be used.

PEG: Poly (ethylene glycol); EDC: 1-ethyl-3-(-3-dimethylaminopropyl) carbodiimide hydrochloride; NHS: N-hydroxysuccinimide; DDI water: double deionized water; PBS: Phosphate-buffered saline; RBD: receptor binding domain of SARS-CoV-2 spike protein

EXAMPLES

The invention is further illustrated by the following examples.

Example 1

Carboxy Functionalized Nanoparticles

To a suspension of 100 nM Au nanoparticles ("GNP"s, NanoComposix, San Diego, Calif.) in 1 mL EtOH was added 1 mL of a solution (10 mM) of 3-mercaptopropionic acid in EtOH. The resulting mixture was incubated in a centrifuge tube several hrs at rt with intermittent shaking and sonication. The mixture was subjected to a final sonication, then centrifuged 5 min at ~5000 RCF, or until particles were sufficiently sedimented. The supernatant was removed, with care taken so as not to disturb the solid pellet. An EtOH rinse was performed as follows: EtOH (1 mL) was added, and the mixture was sonicated to re-suspend the particles. The mixture was centrifuged 5 min at ~5000 RCF, or until particles were sufficiently sedimented. The EtOH rinse was repeated 2 additional times, for a total of 3 EtOH rinses. A water rinse was performed following the procedure of the EtOH rinse, using water in place of EtOH, for a total of 3 water rinses.

Example 2

C2 Anti-CRP Antibody Conjugated Nanoparticles

To an aqueous suspension of the carboxy functionalized nanoparticles (1 mL) was added 20 µL of an aqueous solution containing 10 mg/mL EDC, followed by 40 µL of an aqueous solution containing 10 mL/mg sulfo-NHS. The mixture was incubated for 30 min with rotation, then centrifuged at 5000 RCF for 5 min. The supernatant was removed, with care taken so as not to disturb the solid pellet. To the pellet was added 1 mL of 0.1×PBS, and the particles were re-suspended with vortexing and/or sonication (<30 sec). To the suspension was added 20 µG C2 anti-CRP (C-reactive protein) antibody (Abcam, Cambridge, UK), and the mixture was incubated at rt for 2 hrs, then centrifuged. The supernatant was removed, with care taken so as not to disturb the solid pellet. A PBS rinse was performed as follows: To the pellet was added 1 mL of 0.1×PBS, and the particles were re-suspended with vortexing and/or sonication (<30 sec). The PBS was repeated two additional times, for a total of 3 rinses. On the third and final rinse, 1 mL of 0.1×PBS+0.5% (v/v) Tween 20 was used. The resulting material was stored at 4° C.

Example 3

C6 Anti-CRP Antibody Conjugated Nanoparticles

The procedure for Example 2 was followed, with C6 anti-CRP antibody (Abcam, Cambridge, UK) used in place of C2 anti-CRP antibody.

Example 4

Optical Absorption Studies of Conjugates

Figure 5:
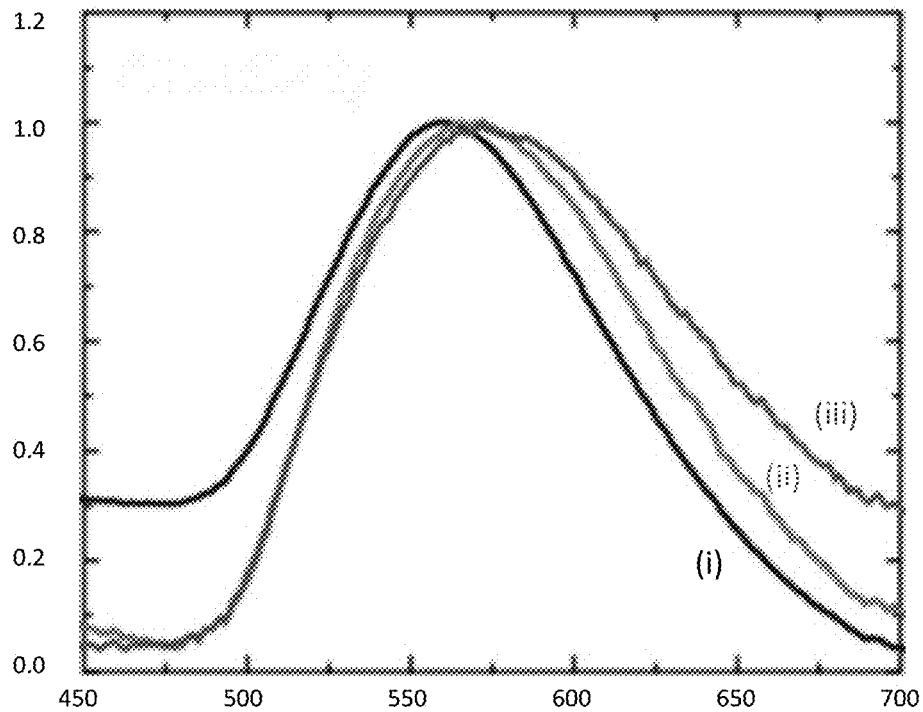
FIG. 5 shows the absorption spectra of gold nanoparticles conjugated with (a) C2 antibody and (b) C6 antibody. (i) bare GNP (gold nanoparticle); (ii) GNP-antibody conjugate; (iii) GNP-antibody conjugate+CRP (C-reactive protein).
Figure 5:
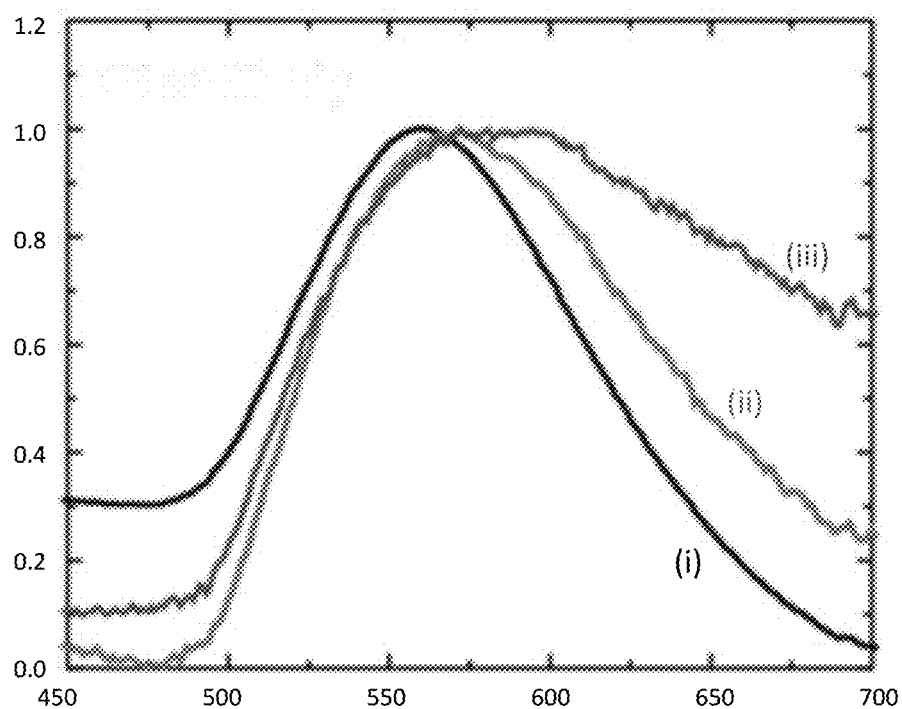

FIG. 5 shows the UV-Vis absorption spectra for suspensions of GNPs (gold nanoparticles) conjugated with C2 antibodies (Panel (a)) and C6 antibodies (Panel (b)). For each conjugate, a slight red shift is observed from bare GNP (i) to GNP-antibody conjugate (ii), due presumably to perturbation of dielectric properties at the GNP, leading to changes in localized surface plasmon resonance (LSRP). For each conjugate, addition of CRP causes a further change in optical absorbance (iii), confirming that the antibodies remain active to capture CRP in solution. A larger change in optical absorbance was observed for the C6 antibody (Panel (b), trace (iii)) than for the C2 antibody (Panel (a), trace (iii)).

Example 5

Aggregation Studies

GNPs conjugated with C2 antibodies and C6 antibodies were combined in a 1:1 ratio, and suspended in PBS+0.05% TWEEN® 20. The detergent was added to stabilize particle suspension. A solution of CRP (10 μL) was then mixed with the solution of GNP-antibody conjugates (20 μL) and incubated at 37° C. for a period of time. After incubation, 15 μL of the CRP/GNP-antibody conjugate mixture was sandwiched between two microscope glasses, forming a thin liquid film. Aggregation behavior was observed using an upright optical microscope in DF mode, typically using a 40× objective. A full-size DF frame typically contains 2,000-10,000 particles within a 250 mm×200 mm area. Use of higher concentrations is expected to increase the degree of overlap for the aggregate frames, complicating signal processing.

Figure 6:
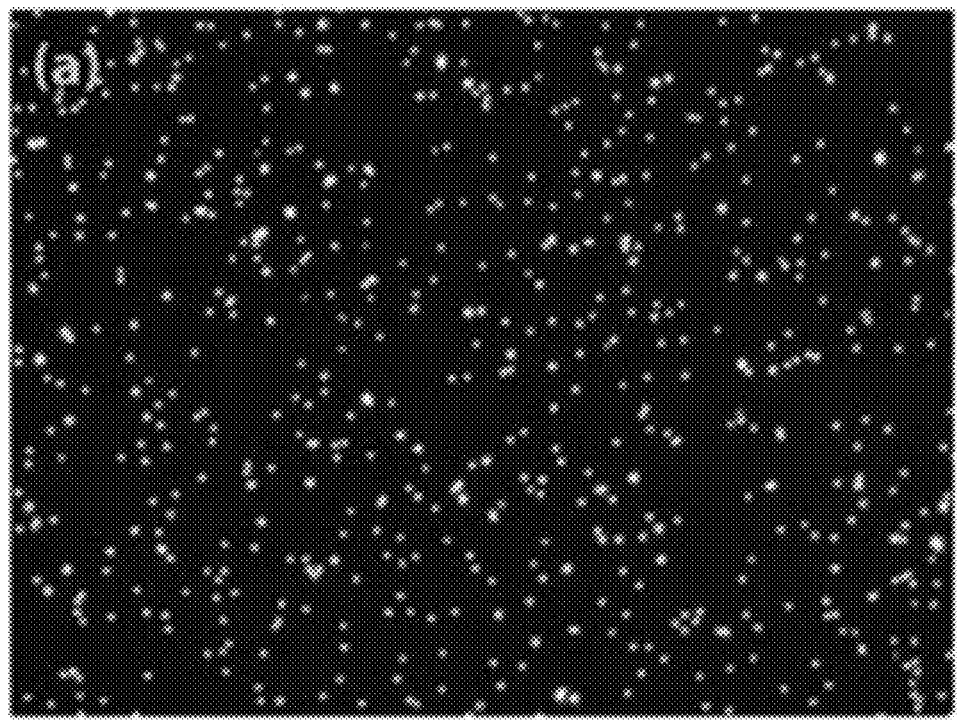
FIG. 6 shows darkfield frames of GNPs. (a) control, in absence of CRP; (b) addition of CRP, showing aggregate formation.
Figure 6:
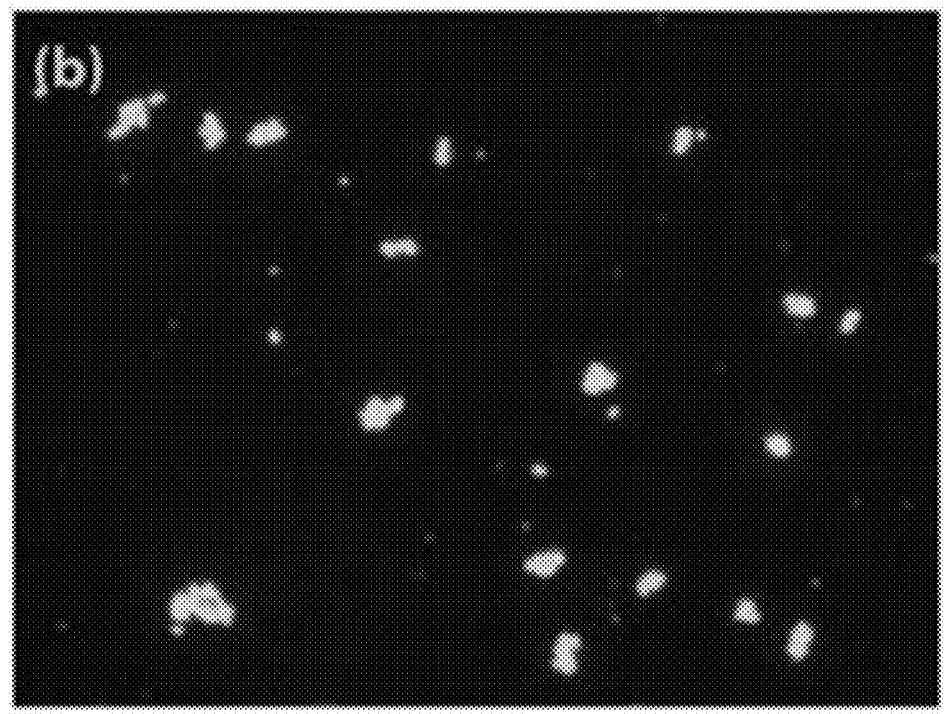
Figure 7:
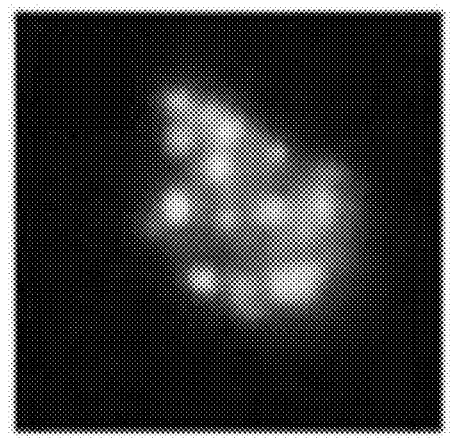
FIG. 7 shows enlarged views of individual clusters.
Figure 7:
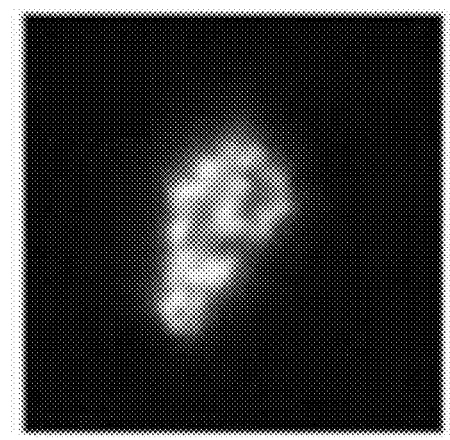
Figure 7:
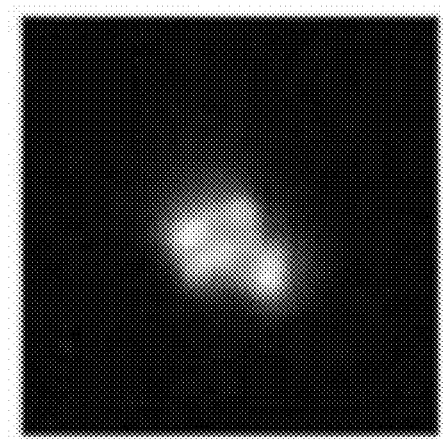

FIGS. 6 and 7 show DF micrographs from controls and positive experiments. In the absence of CRP, individual GNPs are imaged (FIG. 6(*a*)). Addition of CRP leads to the formation of GNP clusters, clearly visible in the micrographs (FIG. 6(*b*)). Individual clusters are imaged in FIGS. 7(*a*)-7(*c*).

A typical experiment consists of 10 frames, requiring analysis of 20,000-100,000 particles. The need to analyze the large number of particles motivated the development of image processing methods, described in Examples 6-9, to automate the procedure and obviate labor-intensive manual evaluation. Factors that were considered for signal processing included: bright circular defects in the frame, due to dust/debris outside the focal plane, the dimmer optical signal from individual GNPs, and the non-uniform shape of aggregates.

Figure 8:
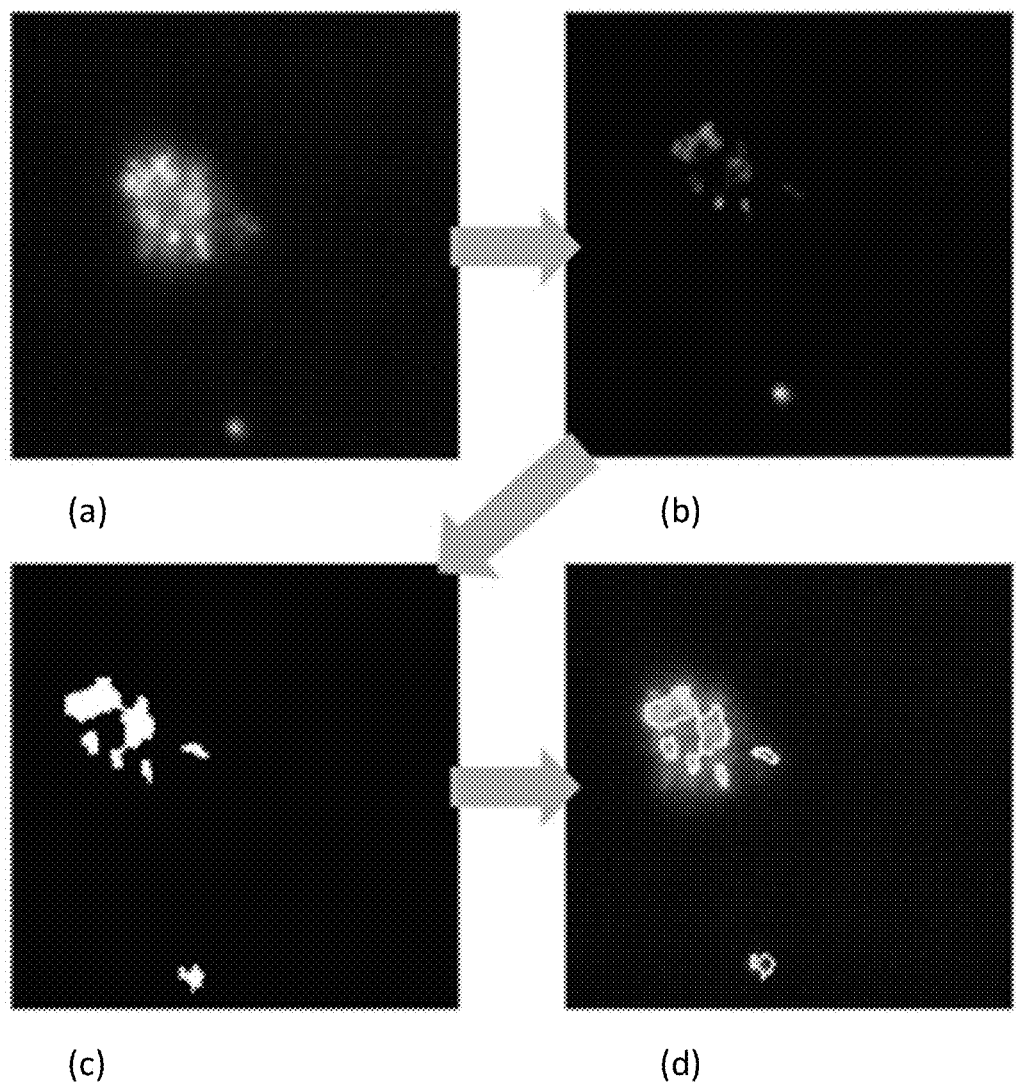
FIG. 8 shows an example of frame processing. (a) original frame; (b) after artifact removal; (c) after object segmentation; (d) quantification of cluster sizes.

An overview of the signal processing method is illustrated in FIG. 8. The original frame, converted to grayscale (Panel (a)), is processed to remove artifacts (Panel (b)). Following this step, the frame is segmented into regions, each of which corresponds to a particle or particle aggregate (Panel (c)). The size of each segment is then quantified (Panel (d)).

Example 6

Subtraction of Signal Background

The following MATLAB code removes background from frames. The code works an frame I indexed by j, and requires the user-supplied bglvl parameter.

```
se = strel('disk',bglvl);         % create a structuring element
Ie = imerode(I{j,1}, se);         % use structuring element to
                                  % identify large background features
% next, a series of functions that optimize the background frame
Iobr = imreconstruct (Ie, I{j,1});
Iobrd = imdilate (Iobr, se);
Iobrcbr = imreconstruct (imcomplement (Iobrd), imcomplement (Iobr));
Iobrcbr = imcomplement (Iobrcbr);   % final background frame
% subtract background frame
i = I{j,1}-Iobrcbr;
```

Figure 9:
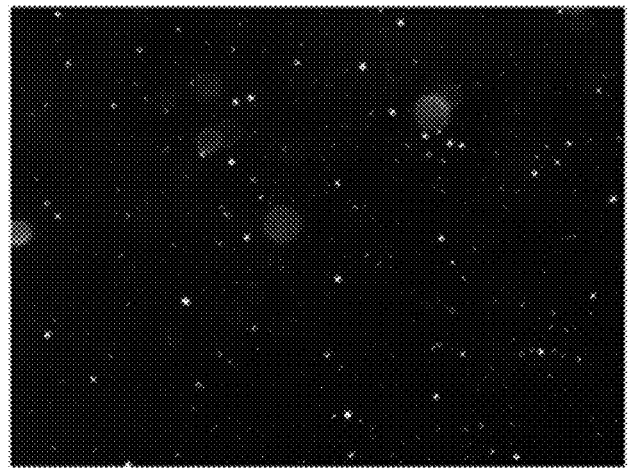
FIG. 9 shows an example of the frame cleaning procedure. (a) original frame; (b) background; (c) cleaned grayscale.
Figure 9:
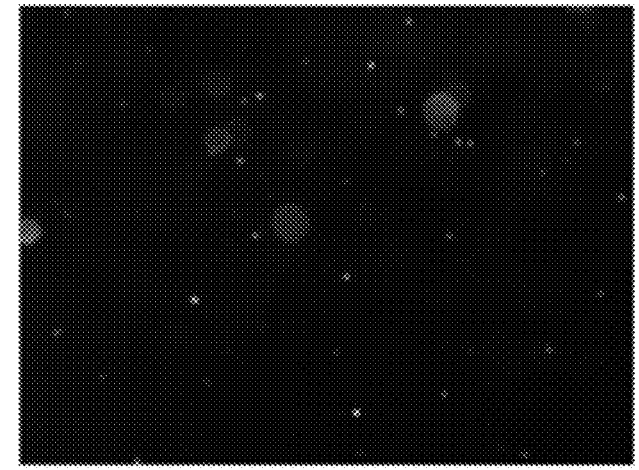
Figure 9:

The effect of this procedure can be seen in FIG. 9. The original frame in Panel (a) is processed to yield background frame (Panel (b)), which is subtracted from the original frame to give background-subtracted Panel (c).

Example 7

Border Formation

The following MATLAB code constructs frames from the cleaned grayscale frames containing B/W features corresponding to individual aggregates. The procedure creates borders at locations of high gradient (i.e. going from black to white rapidly). The gradient magnitude threshold is modified by the user-supplied parameter FudgeFactor. For most analyses, a value of FudgeFactor=1.05 was employed. In order to accommodate features that are not perfectly enclosed by the border produced by this step, the border size is dilated. Then, regions fully enclosed by border are filled in, and the dilation is reversed.

```
[~, threshold] = edge(i, 'sobel');       % find a threshold for edges
BWs = edge(i, 'sobel', threshold * fudgeFactor);
                                         % draw border around object
BWsdil = imdilate (BWs, strel('disk', 1));
                                         % dilate borders
                                         % merges nearby objects,
                                         % connects most borders
BWdfill = imfill (BWsdil, 'holes');      % fills in enclosed regions
BWnobord = imclearborder (BWdfill, 4);   % removes objects at edge
Bwfinal = imerode (Bwnobord, strel('disk', 1));
                                         % undo of prev dilation
```

Figure 10:
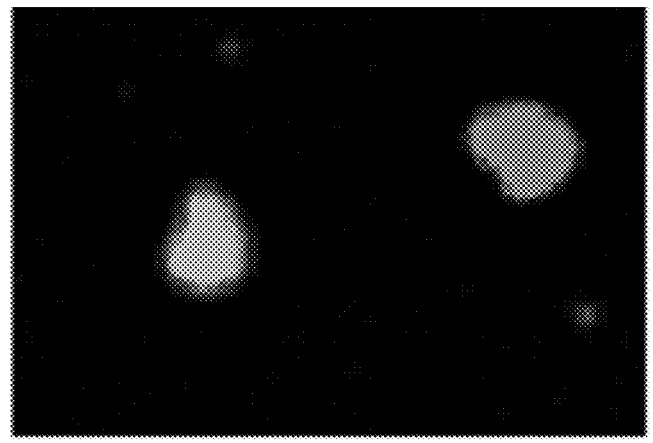
FIG. 10 shows an example of the border formation procedure. (a) cleaned grayscale frame; (b) border frame; (c) B/W frame.
Figure 10:
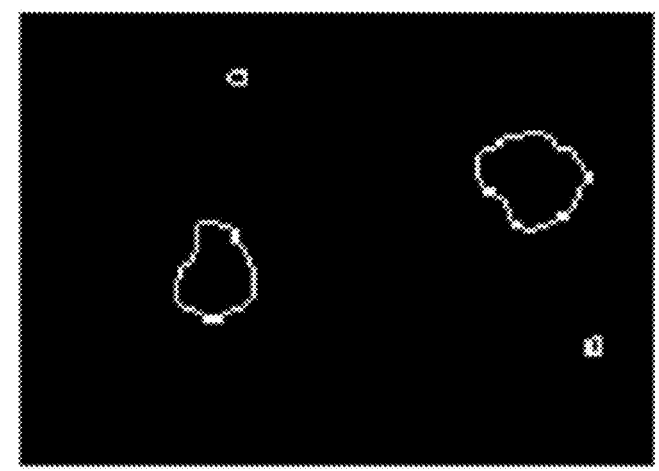
Figure 10:
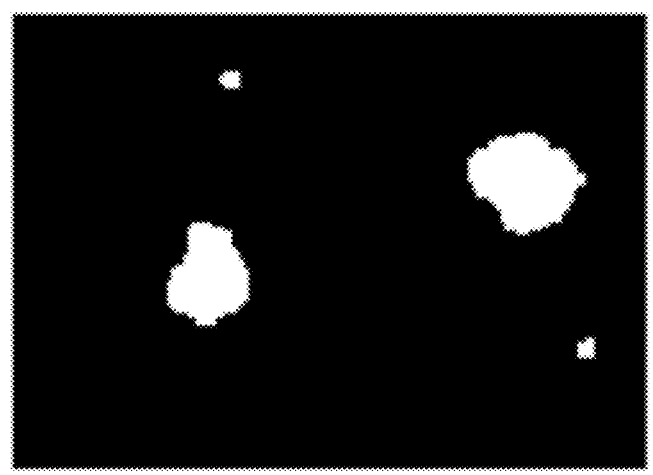

FIG. 10 shows an example of the border formation procedure. The frame cleaned from the background subtraction step, shown in Panel (a), is subjected to the border formation procedure. Panel (b) shows successful identification of borders for the four features on this frame. The borders are then filled in, to provide a B/W frame (Panel (c)) corresponding to the four features.

Example 8

Feature Identification

The following MATLAB code identifies features that correspond to individual aggregates. A vector of features is created from the B/W frame using the MATLAB bwconncomp function. Features that have fewer pixels than a user-supplied parameter T are considered noise and revert to background.

```
s = size (Bwfinal);
BWfinal = BWfinal(ceil(s(1))/8):(floor(7*s(1)/8)-1),
    ceil(s(2))/8):floor(7*s(2)/8-1);    % removes first and last 1/8th
                                        % these regions distorted on frame
CC = bwconncomp(BWfinal, 4);            % constructs list of objects
numPixels = cellfun(@numel, CC.PixelIdxList);
[~,idx] = find(numPixels < T);          % elements having < T pixels
for k = 1:length(idx)
    BWfinal(CC.PixelIdxList{idx(k)}) = 0;
end
```

Figure 11:
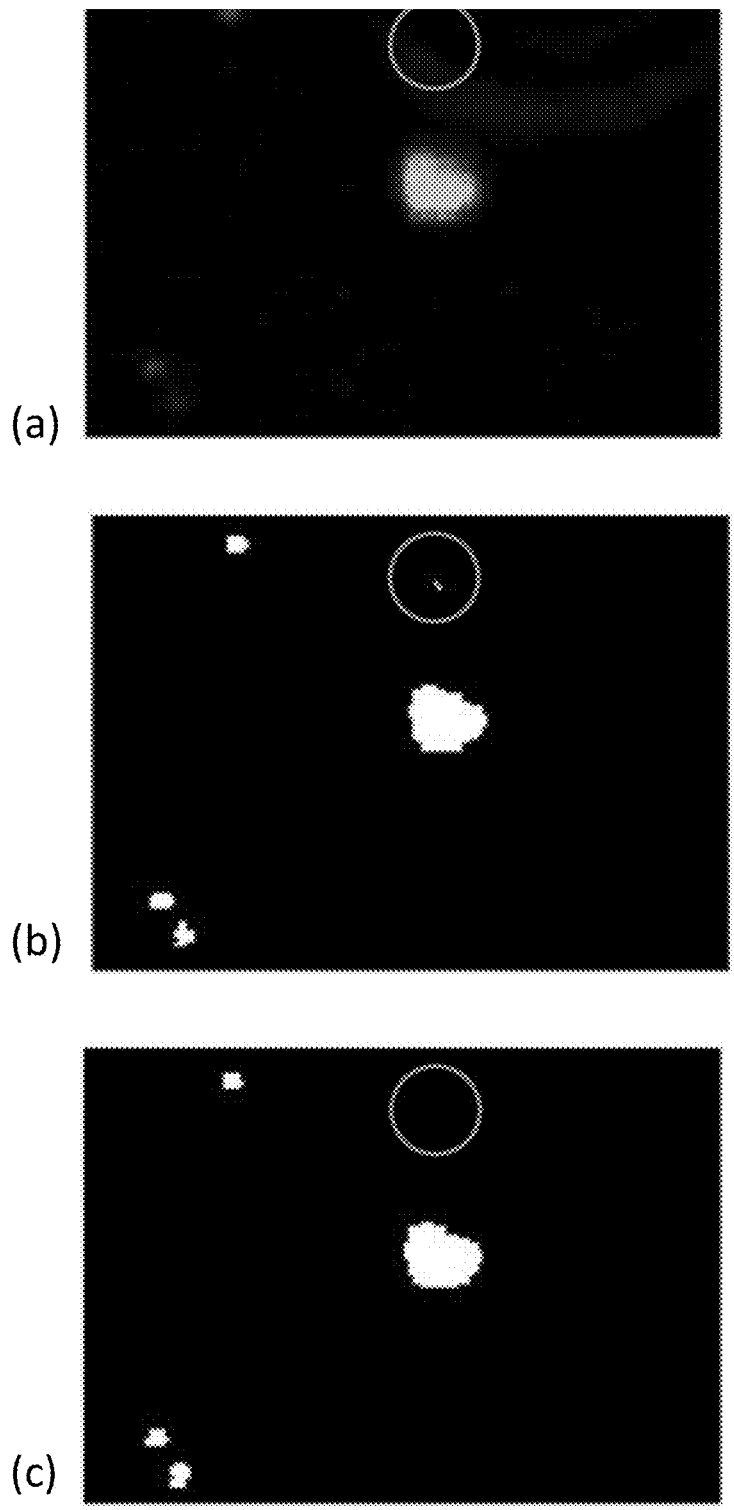
FIG. 11 shows an example of the feature identification procedure. (a) cleaned grayscale frame; (b) B/W frame before noise removal; (c) B/W frame after noise removal.

FIG. 11 shows an example of the feature identification procedure. Panel (a) cleaned grayscale frame before processing. Panel (b) shows B/W frame from the border formation procedure. Panel (c) B/W frame after noise removal. It will be noticed that an artifact, circled in all three panels, has been successfully removed.

Example 9

Frame Padding

The following MATLAB code identifies pads the frame to its original size, for ease in comparison. A label matrix is constructed with elements corresponding to each feature. The area of each feature is calculated and stored.

```
LL = bwlabel(BWfinal,4);         % converts B/W frame to label frame
ss = (s-size(LL))/2;
X.label{j,1} = padarray(LL,floor(ss),0,'both');
                                 % returns array to original size
x = regionprops(X.label{j},'Area');
Areas{j.1} = cell2mat({x.Area});
```

Example 10

CRP Titration

Figure 12:
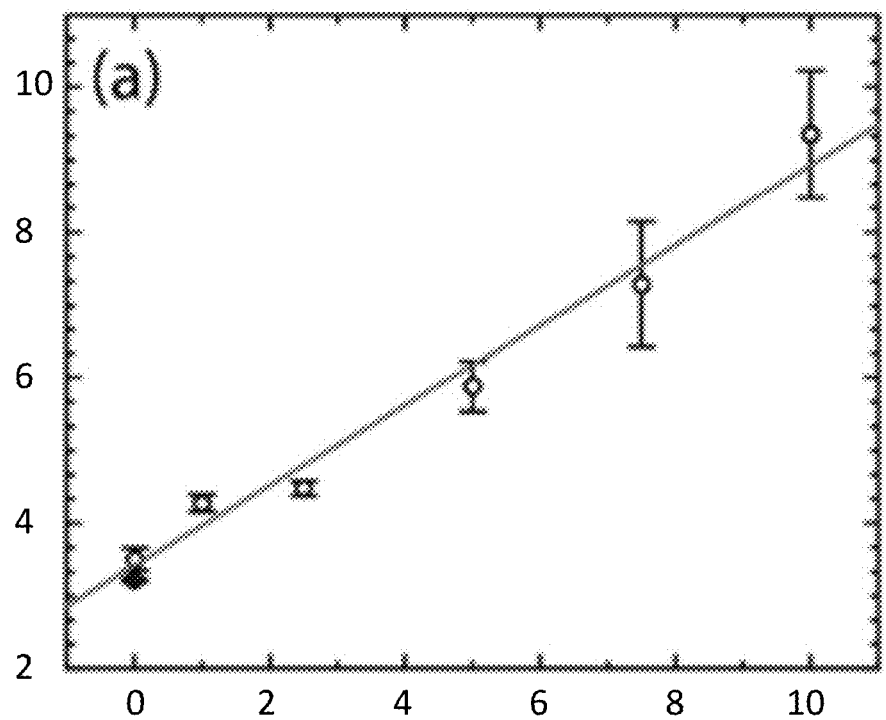
FIG. 12 shows a titration of CRP. (a) aggregation assay with DF detection, horizontal axis=CRP concentration (mg/L), vertical axis=mean aggregate size ($\mu m^2$/cluster); (b) conventional plasmonic sensing, horizontal axis=CRP concentration (mg/L), vertical axis=scattering intensity (A.U.).
Figure 12:
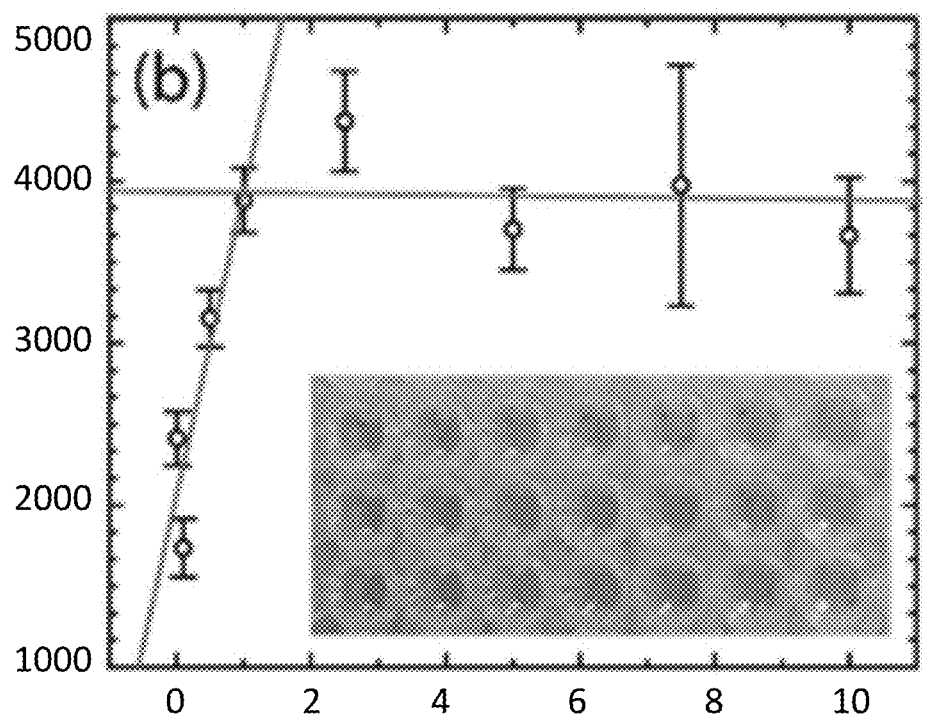

FIG. 12 illustrates a CRP assay, using the disclosed aggregation method, and compared against a conventional plasmon sensing method. The polydispersity of particle clusters leads to noisy responses to analysis of ensemble averages. In contrast, particle-to-particle analysis offers detailed information on particle aggregation, leading to improved sensitivity and dynamic range. Panel (a) shows a calibration curve, derived from analyzing cluster size distribution for a number of CRP concentrations. The linear relationship between mean cluster size and CRP concentration is noteworthy, and contrasts with a conventional plasmon sensing method, shown in Panel (b) which, in contrast, displays the saturation isotherm that is typical for many assays. Importantly, the linear relationship of panel (a) clearly displays significantly different mean cluster sizes for CRP concentrations of 2-3 mg/mL (corresponding to the risk threshold for heart disease) and CRP concentrations of 10 mg/mL (corresponding to normal levels). The conventional plasmon sensing method was unable to distinguish between these two levels.

Example 11

Detection of C-Reactive Protein (CRP) in Whole Blood

Figure 13:
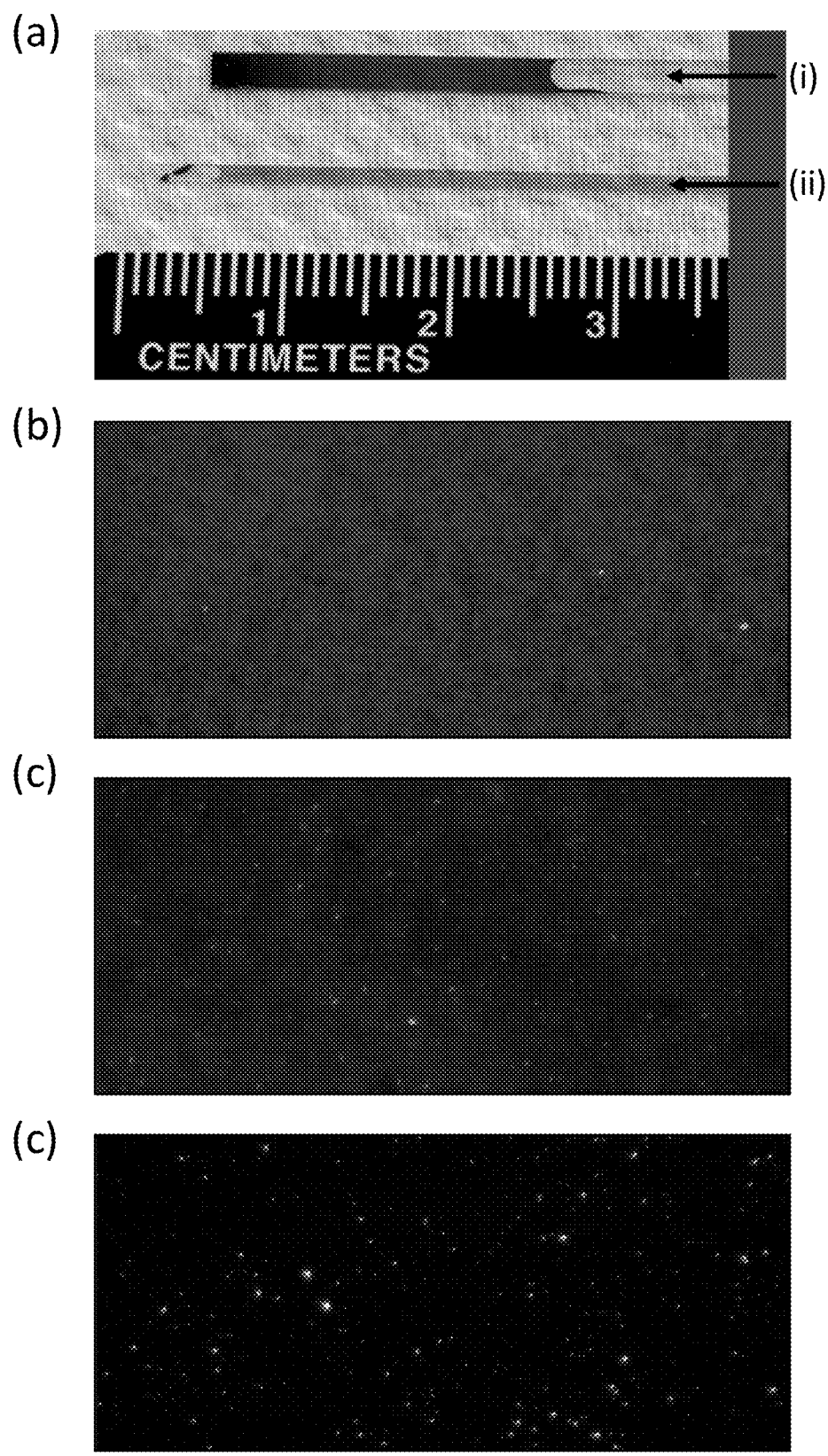
FIG. 13 shows assays performed in whole blood. (a) capillaries in (i) 0.1 mm and (ii) 0.05 mm depth. Also shown are darkfield images of blood in (b) 0.1 mm (c) 0.05 mm and (d) 0.01 mm thick capillaries.

Detection of particles in whole blood is shown in FIG. 13. Capillaries in depths of (i) 0.1 mm and (ii) 0.05 mm are shown in Panel (a). Darkfield images showing particles in whole blood using 0.1 mm, 0.05 mm, and 0.01 mm thick capillaries are shown in Panels (b), (c), and (d), respectively.

Figure 14:
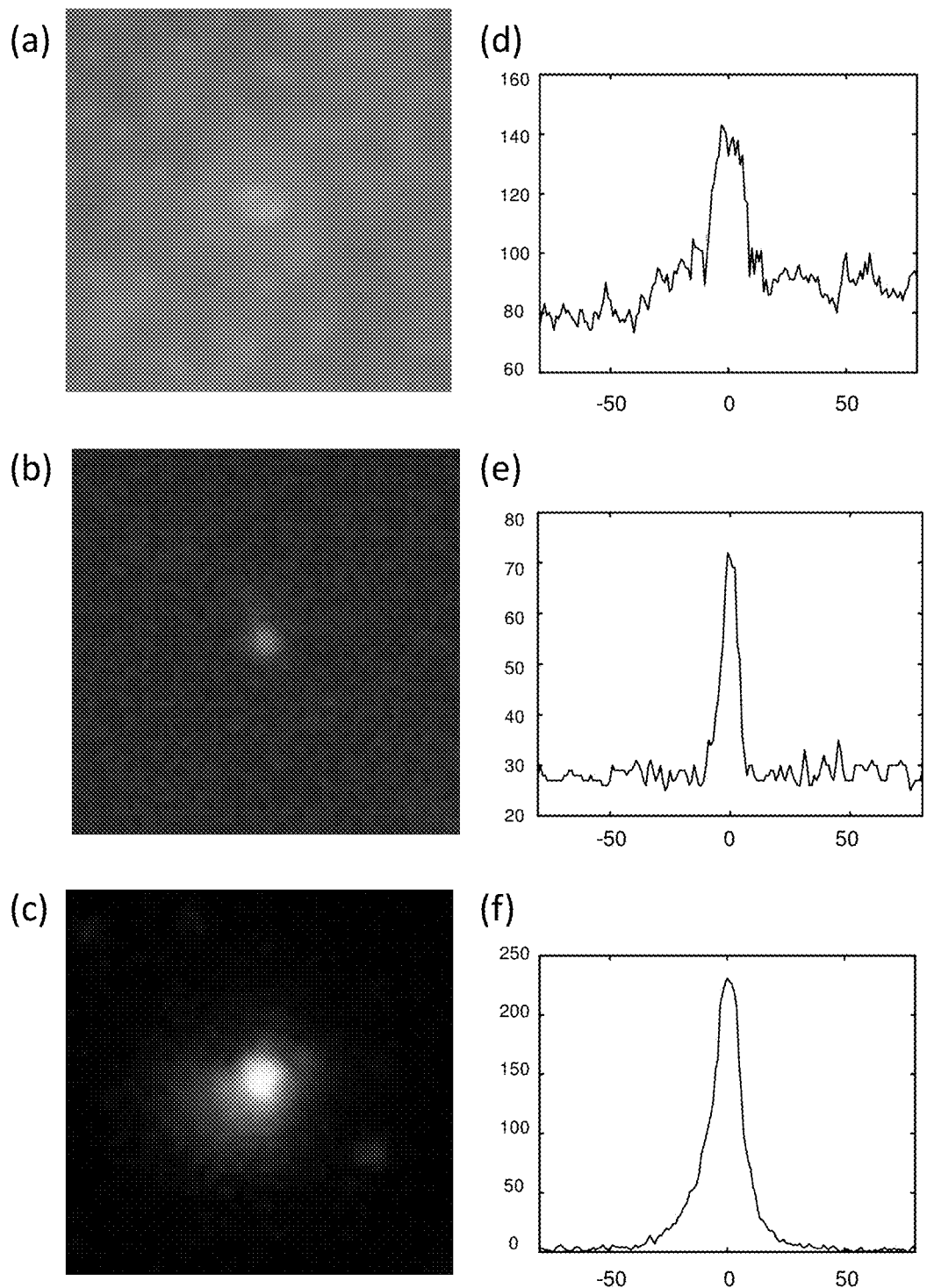
FIG. 14 shows darkfield imaging of nanoparticles in whole blood having imaging depth of (a) 0.11 mm, (b) 0.05 mm, and (c) 0.01 mm. Also shown are intensity (brightness) profiles, horizontal scale=distance in pixels from center of particle, vertical scale=16 bit intensity, for imaging depth of (a) 0.11 mm, (b) 0.05 mm, and (c) 0.01 mm.

Imaging of individual nanoparticles in whole blood of various depths is shown in FIG. 14. Nanoparticles are depicted in media having depths of 0.1 mm, 0.05 mm, and 0.01 mm in Panels (a), (b), and (c), respectively. 16-bit intensity (brightness) plots of these images are shown in Panels (a), (b), and (c), respectively.

Figure 15:
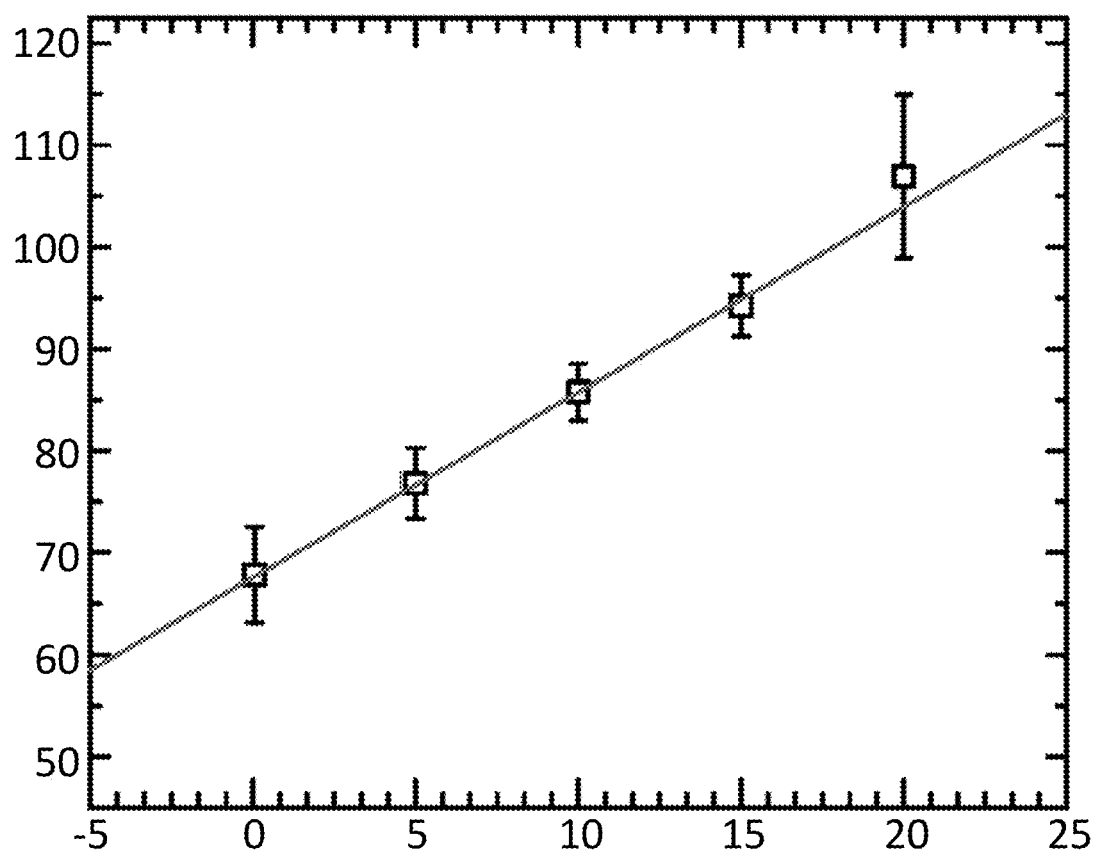
FIG. 15 shows the CRP assay performed in whole blood. Horizontal axis=CRP concentration (mg/dL); vertical axis=average cluster size (pixel).

The performance of the CRP assay in whole blood is shown in the plot of FIG. 15, with the horizontal axis=CRP concentration (mg/dL), and the vertical axis=average cluster size (pixel). As seen in FIG. 12, the assay takes advantage of a linear relationship between analyte concentration and aggregate size.

Example 12

Synthesis of Anti-Human Antibody Nanoparticles

Au nanoparticles functionalized with anti-human antibody were prepared using the method described in Example 2.

Example 13

Synthesis of RBD-Linked Nanoparticles

The following protocol is used to prepare RBD-linked Au nanoparticles for detection of intact SARS-CoV-2 viruses.

Gold nanoparticle 1 mL PEGylated 80 nm gold nanoparticle solution (20 OD=1.3E11 particle/mL). (Nanocomposix. Bio ready, Carboxyl, 20 OD, SKU: AUXR80-5M) Scale as needed.

RBD Thermo Fisher Scientific, SARS-CoV-2 Spike Protein (S-RBD) (aa319-541), His Tag Recombinant Protein.

Other Chemicals EDC, NHS, DDI water, PBS buffer, $KH_2PO_4$, 20 KDa PEG (Recommended), Glycine (Or Tris Buffer), Tween 20.

A solution containing 10 mg/mL of EDC was prepared by dissolving 1-10 mg of EDC in water. Similarly, a solution containing 10 mg/mL of and sulfo-NHS was prepared by dissolving 1-10 mg sulfo-NHS in water. For both solutions, 100 μL $H_2O$ per mg solute was used, and the solutions were prepared immediately prior to use.

To 1 mL of the —COOH-terminated particles (suspended in DDI water) was added 7 μL of the EDC solution, followed by 14 μL of the sulfo-NHS solution. The solution was mixed well, then incubated at room temperature for 30 minutes on a tube rotator. The solution was centrifuged at 5000 RCF for 5 minutes. The supernatant liquid was carefully removed, 1 mL of reaction buffer (5 mM $KH_2PO_4$+0.5% (v/v) 20 KDa PEG at pH 7.4) was added. The mixture was vortexed and sonicated (<30 seconds) to resuspend particles. To the mixture was added 20 μL of 1 mg/mL RBD protein, and the mixture was vortexed to mix, and incubated at room temperature for 2 hours. To the mixture was then added 5 μL saturated glycine (in DDI Water), and the contents were mixed and incubated for 10 minutes.

The particles were washed with reaction buffer as follows: The mixture was centrifuged at 5000 RCF for 5 minutes, the supernatant liquid was removed, and the pellet was resuspended with 1 mL reaction buffer, using 30 sec or less of sonication. The reaction buffer rinse was repeated two additional times, for a total of 3 rinses. On the third and final rinse, the pellet was resuspended in 1 mL of 0.1×PBS+0.5% (v/v) Tween 20. The resulting material was stored at 4° C.

The following sequence was used to refill the particle surface with PEG, in order to avoid non-specific aggregation. A solution of 2 mg of SH-PEG-COOH (MW 6000) in 50 mL of 0.1×PBS was prepared. Equal volumes of this solution and a solution of conjugated particles and PEG solution were mixed, and incubated for 6 hours with shaking at 25° C. or, alternatively, overnight at 4° C.

The particles were washed with reaction buffer as follows: The mixture was centrifuged at 5000 RCF for 5 minutes, the supernatant liquid was removed, and the pellet was resuspended with 1 mL 0.1×PBS+0.5% (v/v) Tween 20. The reaction buffer rinse was repeated two additional times, for a total of 3 rinses. The resulting material was stored at 4° C.

Example 14

Detection of SARS-CoV-2 Antibody in Whole Blood

Figure 16:
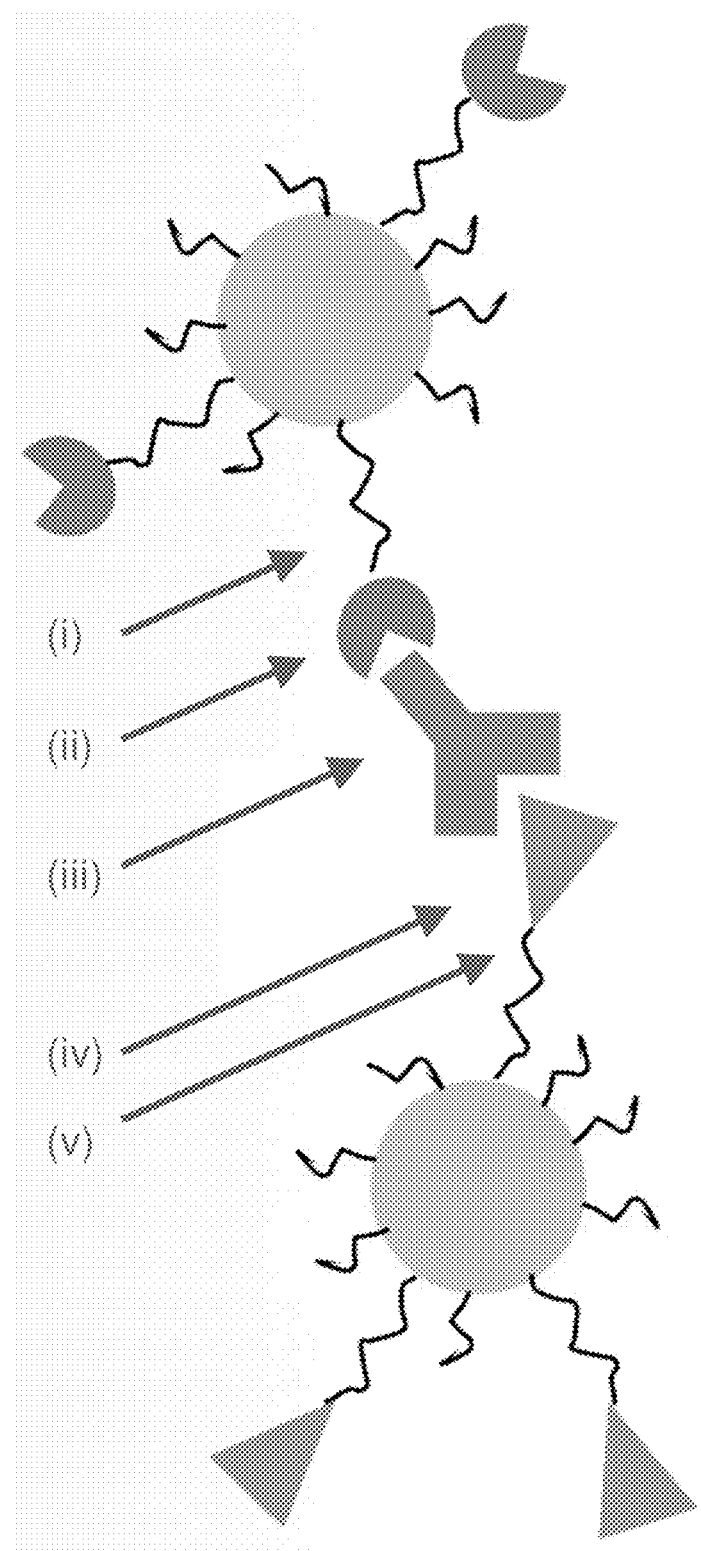
FIG. 16 shows the design principle for detection of the SARS-CoV-2 antibody, illustrated schematically as (iii). (i) and (v) correspond to PEG linkers from Au nanoparticles to (ii) anti-human antibody and (iv) SARS-CoV-2 spike RBD, respectively.

The following assay was developed to detect and quantify antibodies to SARS-CoV-2 Spike Protein. The design principle is illustrated in FIG. 16. The nanoparticles of Example 12 are shown with the anti-human antibody (ii) linked via PEG (i) to a nanoparticle. The nanoparticles of Example 13 are shown with the RBD domain (iv) linked via PEG (v) to a nanoparticle. The analyte (iii), i.e. antibody to SARS-CoV-2 Spike Protein, can bind simultaneously to the two types of functionalized nanoparticles.

Chemicals Antibody: SARS-CoV-2 Spike Protein 51 Chimeric Recombinant Human Monoclonal Antibody (H6)

Whole blood ZenBio, Inc., Cat No: SER-WB10ML

A whole blood sample was prepared with the desired antibody concentration. A solution containing 10 μL of the RBD conjugated particles (20 OD=1.3E11 Particle/mL) and 10 μL of 0.1×PBS+0.5%(v/v) Tween 20 solution was prepared. 20 μL of the diluted particle solution (10 OD=6.5E10 Particles/mL) was mixed with 5 μL of the whole blood sample, and the mixture was vortexed gently, then incubated for 1 hour at 25° C.

A 5 μL of the solution was applied to a large glass slide (CORNING cover glass, thickness 1, 24×50 mm, Cat. No. 2975-245), covered with small cover glass (CORNING cover glass, thickness 1, 18×18 mm, Cat. No. 2845-18). Dark field images were recorded using a 20× objective lens. The images were processed using the home-built image analysis program.

Figure 17:
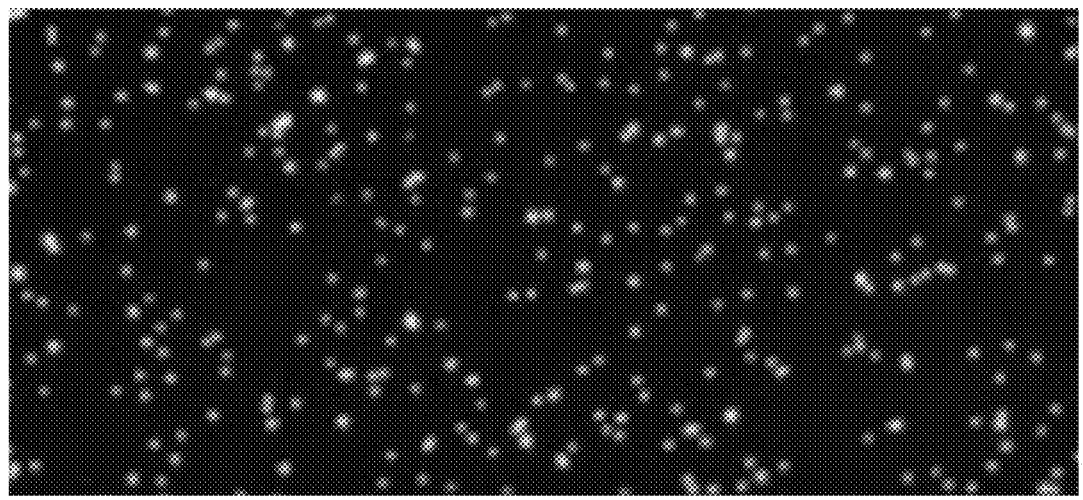
FIG. 17 shows the SARS-CoV-2 assay performed in whole blood. (a) Microscopy of aggregates; (b) calibration curve: horizontal axis=SARS-CoV-2 antibody (mg/dL), vertical axis=aggregation size (pixels).
Figure 17:
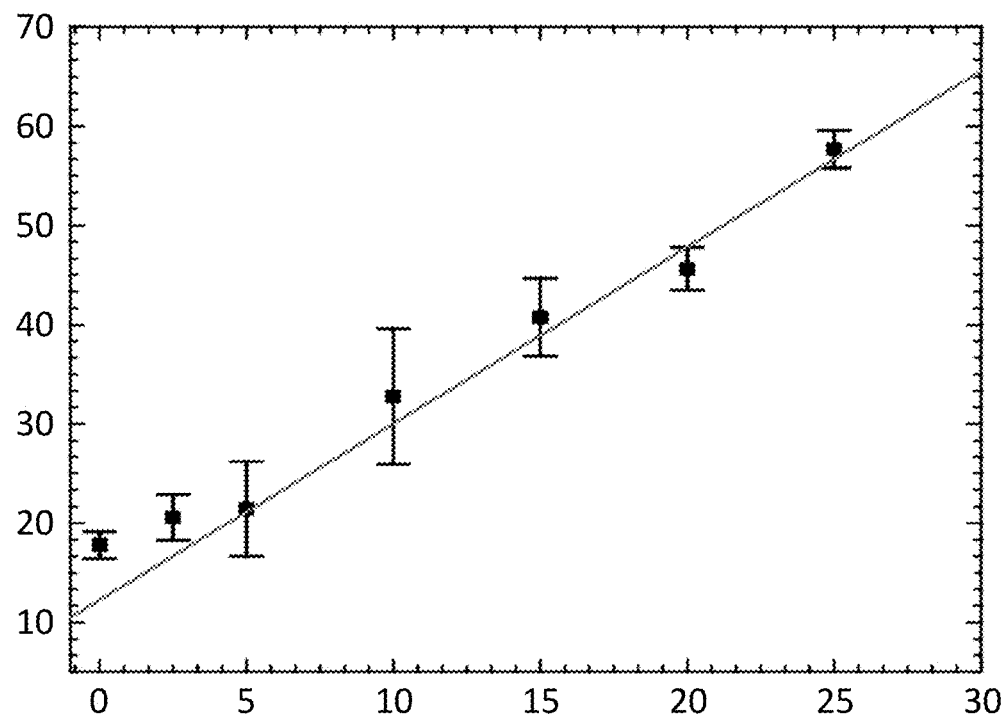

The results of the assay are illustrated in FIG. 17. Panel (a) shows microscopy of aggregates. Panel (b) provides a calibration curve: horizontal axis=SARS-CoV-2 antibody (mg/dL), vertical axis=aggregation size (pixels). Good linearity is observed for antibody concentrations above 5 mg/dL. It will be noted that the COVID-19 IgG concentrations in patient sera are between 0.14 and 420 mg/dL, corresponding to between 1.4 and 4200 μg/ml. Furthermore, 10 mg/dL (or 100 μg/mL) is the cut-off concentration to qualify a donor for convalescent serum therapy.

Example 15

Detection of Intact SARS-CoV-2 Viruses

Figure 18:
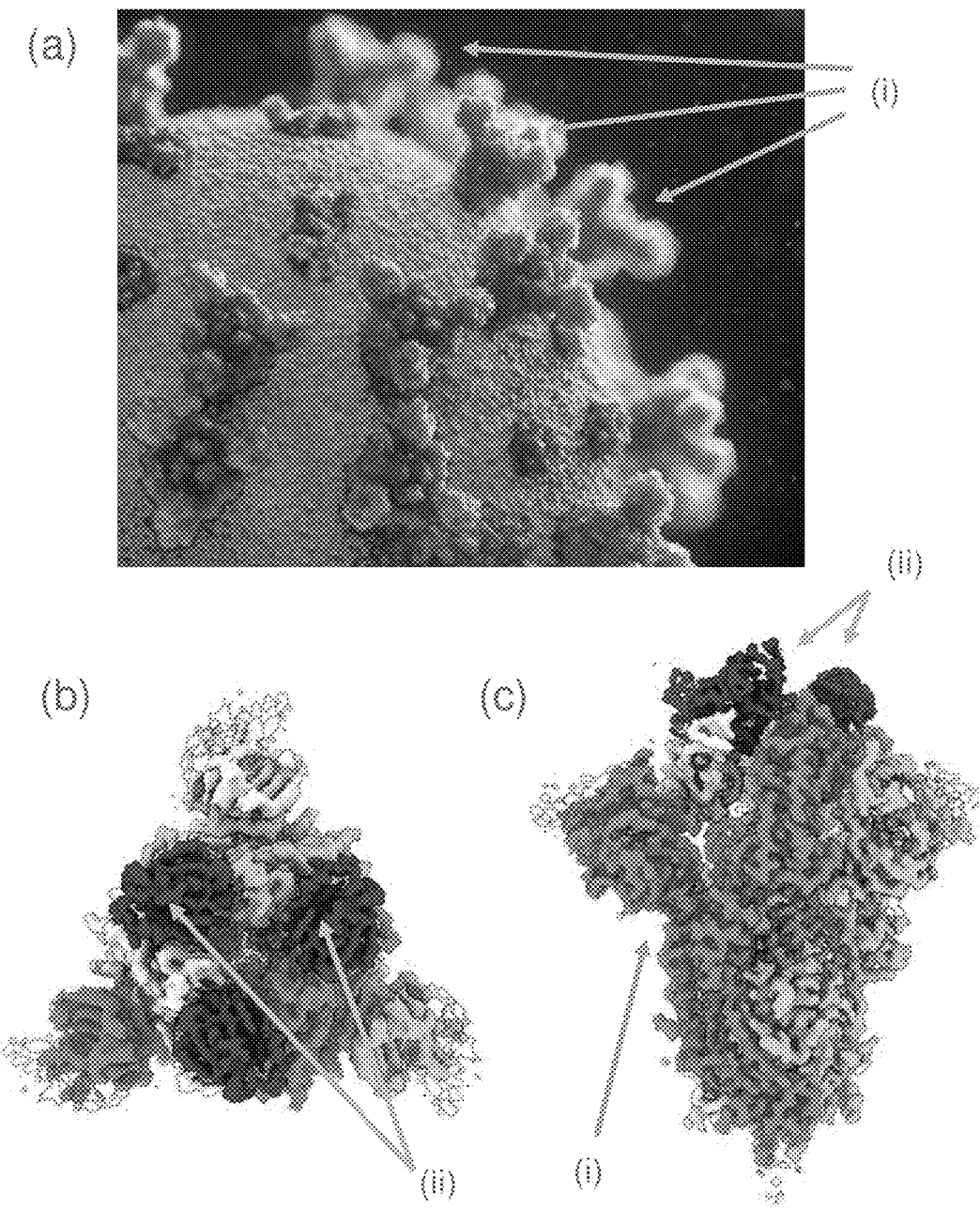
FIG. 18 shows components for the direct viral detection assay. (a) Detail of coronavirus, highlighting (i) multiplicity of spike proteins. (b) Top and (c) side views for interaction between three-part nanobody (ii) and spike protein (i).

The components utilized for the assay for detection of intact SARS-CoV-2 are illustrated in FIG. 18. Panel (a) shows a detail of coronavirus, highlighting (i) multiplicity of spike proteins which decorate the surface of the virus, and which are responsible for cellular invasion. Nanobodies have been designed by others for binding to the spike protein. Panels (b) and (c) show top and side views depicting the interaction between three-part nanobody (ii) and spike protein (i).

Figure 19:
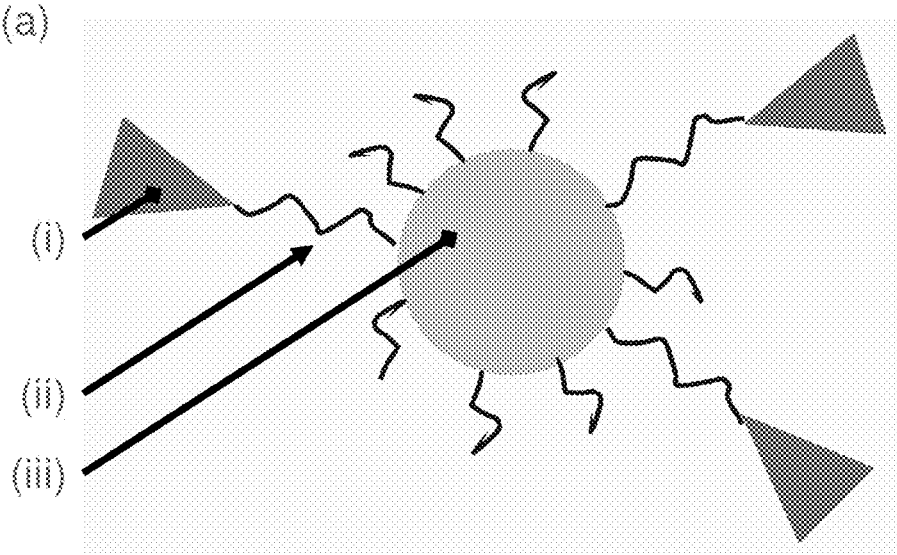
FIG. 19 shows detection of SARS-CoV-2 viruses. (a) Design principle: (i) SARS-CoV-2 spike nanobody (ii) PEG linker (iii) Au nanoparticle. (b) and (c) microscopy of aggregates at various levels of virus concentration. The aggregation mechanism that has been described elsewhere for smaller biomolecules is clearly operative for intact viruses.
Figure 19:
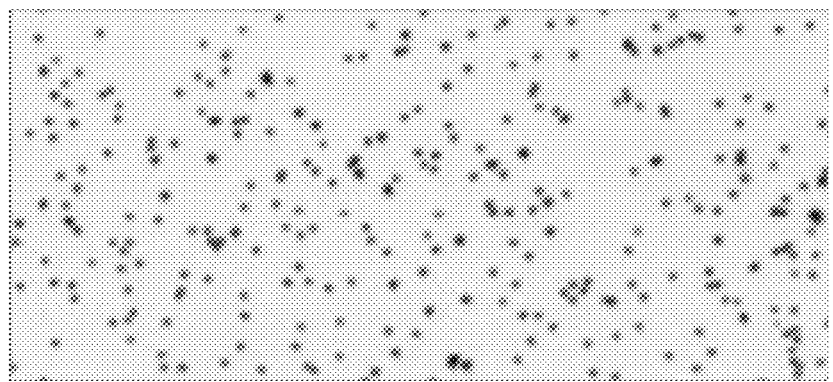
Figure 19:
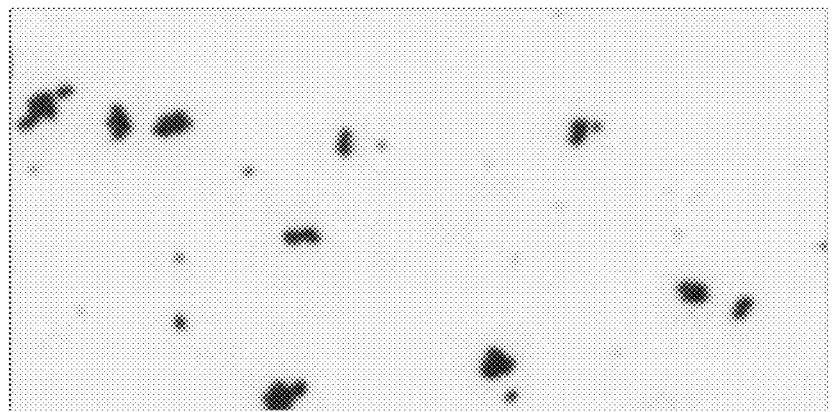

Nanoparticles functionalized with the nanobodies for the SARS-CoV-2 spike protein have been prepared using the method described in Example 2. Details of the detection of SARS-CoV-2 are illustrated in FIG. 19 shows detection of SARS-CoV-2 viruses. Panel (a) shows the nanobody-functionalized nanoparticle: (i) SARS-CoV-2 spike nanobody (ii) PEG linker (iii) Au nanoparticle. Panels (b) and (c) show microscopy of aggregates at various levels of virus concentration.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for determining a concentration of an analyte particle in a sample comprising the analyte particle and a quantity of one or more types of reporter particles, wherein the presence of analyte particle induces the formation of aggregates, each comprising at least two reporter particles and at least one analyte particle, comprising the steps of:
    performing, in one or more recorded frames of a detector volume comprising the sample, one or more steps of border formation, comprising converting the one or more recorded frames to grayscale and creating borders at locations of high gradient;
    identifying, in the one or more recorded frames, images of particles corresponding to aggregates of reporter particles and, optionally, individual un-aggregated reporter particles, wherein each of the one or more recorded frames comprises between 2,000 and 10,000 particles;
    determining one or more object characteristics of the particles corresponding to aggregates, wherein mean aggregate size can be determined from the object characteristics; and
    from the object characteristics, determining the concentration of the analyte particle.

2. The method as recited in claim 1, wherein formation of aggregates is caused by binding between a binding site on the reporter particle and a binding site on the analyte particle.

3. The method as recited in claim 1, wherein the object characteristic increases monotonically with mean aggregate size.

4. The method as recited in claim 1, wherein the reporter particle provides an optical signal.

5. The method as recited in claim 4, wherein the optical signal is caused by surface plasmon resonance.

6. The method as recited in claim 1, further comprising the step of removing background features.

7. The method as recited in claim 6, further comprising the step of removing background features greater than a given size maximum.

8. The method as recited in claim 6, further comprising the step of removing background features smaller than a given size minimum.

9. The method of claim 6, further comprising the steps of:
    eroding an image;
    reconstructing an image; and
    dilating an image.

10. The method as recited in claim 1, wherein the reporter particle comprises a nanoparticle or quantum dot.

11. The method as recited in claim 1, wherein each of the one or more types of reporter particles present in the quantity of reporter particles contains one or more binding sites of the same type.

12. The method as recited in claim 11, wherein:
    the one or more types of reporter particles is a single type of reporter particle;
    the single type of reporter particle can bind simultaneously to two or more analyte particles; and
    the analyte particle can bind simultaneously to two or more reporter particles.

13. The method as recited in claim 11, wherein:
    the one or more types of reporter particles are two types of reporter particles;
    each of the two types of reporter particles contains a different type of binding site from the other type of reporter particle;
    each of the two types of different binding sites on the two types of reporter particles bind to a different binding site on the analyte particle;
    each of the two types of reporter particles can bind simultaneously to two or more analyte particles; and the analyte particle can bind simultaneously to one or more of each of the two types of reporter particles.

14. The method as recited in claim 13, wherein each of the two types of different binding sites is located on an antibody or nanobody contained in each of the two types of reporter particle.

15. The method as recited in claim 1, wherein the analyte is an antibody.

16. The method as recited in claim 15, wherein the analyte is an antibody to a biomolecule in the viral envelope of a virus.

17. The method as recited in claim 16, wherein the biomolecule is a protein in the viral envelope chosen from a membrane protein, an envelope protein, and a spike protein.

18. The method as recited in claim 1, wherein the analyte is a hematological protein.

19. The method as recited in claim 18, wherein the hematological protein is C-reactive protein.

20. The method as recited in claim 1, wherein the sample is a biological fluid.

21. The method as recited in claim 1, wherein the sample is derived from a biological fluid.

22. The method as recited in claim 1, wherein the sample is analyzed with a microscope capable of darkfield imaging.

23. The method as recited in claim 22, wherein the sample is processed with a microfluidic apparatus.

* * * * *